US012168140B1

(12) United States Patent
Chalifoux

(10) Patent No.: US 12,168,140 B1
(45) Date of Patent: Dec. 17, 2024

(54) APPARATUS FOR NEURAL STIMULATION AND METHOD OF USE

(71) Applicant: Photigen, Inc., Wilmington, DE (US)

(72) Inventor: Joseph Chalifoux, Nashua, NH (US)

(73) Assignee: Photigen, Inc., Wilmington, DE (US)

( * ) Notice: Subject to any disclaimer, the term of this patent is extended or adjusted under 35 U.S.C. 154(b) by 0 days.

(21) Appl. No.: 18/212,117

(22) Filed: Jun. 20, 2023

(51) Int. Cl.
*A61N 2/00* (2006.01)
*A61N 5/06* (2006.01)
(Continued)

(52) U.S. Cl.
CPC .............. *A61N 2/002* (2013.01); *A61N 2/006* (2013.01); *A61N 5/0618* (2013.01); *A61N 7/00* (2013.01); *G06F 1/163* (2013.01); *G06N 20/00* (2019.01); *A61N 2005/0648* (2013.01); *A61N 2005/0663* (2013.01); *A61N 2007/0026* (2013.01); *H04R 1/22* (2013.01)

(58) Field of Classification Search
CPC .................... A61N 2/002; A61N 2/006; A61N 2005/0648; A61N 2005/0663; A61N 2007/0026; A61N 5/0618; A61N 7/00; G06F 1/163; G06N 20/00; H04R 1/22
See application file for complete search history.

(56) References Cited

U.S. PATENT DOCUMENTS 4,315,502 A  2/1982 Gorges
4,858,609 A  8/1989 Cole
(Continued)

FOREIGN PATENT DOCUMENTS

WO  2017091698 A1  6/2017
WO  2018094226 A1  5/2018
(Continued)

OTHER PUBLICATIONS

Kasteleijn-Nolst Trenite, et al., "Photic Stimulation: Standardization of Screening Methods," Epilepsia, 1999, vol. 40, pp. 75-59.
(Continued)

*Primary Examiner* — Christine H Matthews
*Assistant Examiner* — Marc D. Honrath
(74) *Attorney, Agent, or Firm* — Greenberg Traurig LLP; Melissa Hunter-Ensor; Nicholas R. Ballor

(57) ABSTRACT

An apparatus for neural stimulation, the apparatus comprising a head device configured to be worn on a head of a user, the head device comprising a light-emitting device configured to provide photic entertainment to the user, and a control module connected to the light-emitting device and configured to operate the light-emitting device through receipt of one or more stimulatory commands, and a computing device communicatively connected to the head device, the computing device comprising a processor, and a memory communicatively connected to the processor, the memory containing instructions configuring the processor to receive user data, wherein the user data comprises information relating to a neural state of a user, generate the one or more stimulatory commands as a function of the user data wherein generating or more stimulatory commands includes determining the neural state of the user, and transmit one or more stimulatory commands to the head device.

17 Claims, 7 Drawing Sheets

(51) Int. Cl.
*A61N 7/00* (2006.01)
*G06F 1/16* (2006.01)
*G06N 20/00* (2019.01)
*H04R 1/22* (2006.01)

(56) References Cited

U.S. PATENT DOCUMENTS

| | | | |
|---|---|---|---|
| 4,940,323 A | 7/1990 | Downing | |
| 6,135,117 A | 10/2000 | Campbell et al. | |
| 9,302,069 B2 | 4/2016 | Tass et al. | |
| 9,950,189 B1* | 4/2018 | Morries | A61B 6/501 |
| 10,159,816 B2 | 12/2018 | Tsai et al. | |
| 10,265,497 B2 | 4/2019 | Tsai et al. | |
| 10,279,192 B2 | 5/2019 | Malchano et al. | |
| 10,293,177 B2 | 5/2019 | Malchano et al. | |
| 10,307,611 B2 | 6/2019 | Malchano et al. | |
| 10,376,710 B2 | 8/2019 | Hebert et al. | |
| 10,448,883 B2 | 10/2019 | Grossman et al. | |
| 10,682,490 B2 | 6/2020 | Tsai et al. | |
| 10,702,705 B2 | 7/2020 | Malchano et al. | |
| 10,758,175 B2 | 9/2020 | Grossman et al. | |
| 10,843,006 B2 | 11/2020 | Malchano et al. | |
| 10,960,225 B2 | 3/2021 | Adaikkan et al. | |
| 11,141,604 B2 | 10/2021 | Malchano et al. | |
| 11,166,632 B2 | 11/2021 | Grossman et al. | |
| 11,241,586 B2 | 2/2022 | Tsai et al. | |
| 11,318,278 B2 | 5/2022 | Grossman et al. | |
| 11,612,757 B1* | 3/2023 | Comito | G16H 20/30 600/13 |
| 2009/0005837 A1 | 1/2009 | Olmstead | |
| 2014/0058483 A1 | 2/2014 | Zao et al. | |
| 2016/0067087 A1 | 3/2016 | Tedford et al. | |
| 2016/0235983 A1* | 8/2016 | Berman | A61N 2/006 |
| 2017/0020447 A1 | 1/2017 | Grossman et al. | |
| 2017/0143934 A1 | 5/2017 | Tsai et al. | |
| 2017/0304584 A1 | 10/2017 | Tsai et al. | |
| 2018/0133431 A1 | 5/2018 | Malchano et al. | |
| 2018/0133504 A1 | 5/2018 | Malchano et al. | |
| 2018/0133507 A1 | 5/2018 | Malchano et al. | |
| 2019/0105509 A1 | 4/2019 | Tsai et al. | |
| 2019/0110754 A1* | 4/2019 | Rao | G06N 7/00 |
| 2019/0126062 A1 | 5/2019 | Adaikkan et al. | |
| 2019/0142636 A1 | 5/2019 | Tedford et al. | |
| 2019/0143073 A1 | 5/2019 | Grossman et al. | |
| 2019/0240443 A1 | 8/2019 | Tsai et al. | |
| 2019/0255350 A1 | 8/2019 | Malchano et al. | |
| 2019/0269936 A1 | 9/2019 | Malchano et al. | |
| 2019/0314641 A1 | 10/2019 | Malchano et al. | |
| 2020/0139112 A1 | 5/2020 | Aharonovitch | |
| 2020/0316334 A1 | 10/2020 | Tsai et al. | |
| 2020/0316335 A1 | 10/2020 | Tsai et al. | |
| 2021/0121713 A1 | 4/2021 | Malchano et al. | |
| 2021/0260404 A1* | 8/2021 | Kosson | A61B 5/4836 |
| 2021/0339043 A1 | 11/2021 | Malchano et al. | |
| 2022/0008746 A1 | 1/2022 | Malchano et al. | |
| 2022/0040496 A1 | 2/2022 | Adaikkan et al. | |
| 2022/0107880 A1* | 4/2022 | Neumann | G06N 20/00 |
| 2022/0151864 A1 | 5/2022 | Tsai et al. | |
| 2022/0233879 A1 | 7/2022 | Tsai et al. | |
| 2023/0022546 A1* | 1/2023 | Malchano | A61N 1/36025 |
| 2023/0104621 A1* | 4/2023 | Malchano | A61N 5/0622 600/544 |
| 2023/0111776 A1 | 4/2023 | Malchano et al. | |
| 2023/0166072 A1 | 6/2023 | Malchano et al. | |
| 2023/0173295 A1 | 6/2023 | Kim et al. | |
| 2023/0181905 A1 | 6/2023 | Tsai et al. | |
| 2023/0218854 A1* | 7/2023 | Fung | G06F 1/1688 600/9 |
| 2024/0269481 A1 | 8/2024 | Malchano et al. | |
| 2024/0293680 A1 | 9/2024 | Malchano et al. | |

FOREIGN PATENT DOCUMENTS

| | | | |
|---|---|---|---|
| WO | 2018094230 A2 | 5/2018 | |
| WO | 2018094232 A1 | 5/2018 | |
| WO | 2018094230 A3 | 7/2018 | |
| WO | 2019074637 A1 | 4/2019 | |
| WO | 2019075094 A1 | 4/2019 | |
| WO | 2022027030 A1 | 2/2022 | |
| WO | WO-2022077439 A1 * | 4/2022 | A61N 7/00 |
| WO | 2022192277 A1 | 9/2022 | |
| WO | 2023049467 A1 | 3/2023 | |
| WO | 2023049470 A1 | 3/2023 | |
| WO | 2023108170 A2 | 6/2023 | |
| WO | 2023177907 A1 | 9/2023 | |
| WO | 2023196610 A1 | 10/2023 | |

OTHER PUBLICATIONS

Chiang, et al., "Seizure suppression by high frequency optogenetic stimulation using in vitro and in vivo animal models of epilepsy," Brain Stimulation, Jul. 18, 2014, vol. 7, No. 6, pp. 890-899.

Noda, et al., "Photobiological Neuromodulation of Resting-State EEG and Steady-State Visual-Evoked Potentials by 40 Hz Violet Light Optical Stimulation in Healthy Individuals," Journal of Personalized Medicine, Jun. 15, 2021, vol. 11, No. 6, pp. 1-19.

Vartanian, et al., "Using Flickering Light to Enhance Nonimage-Forming Visual Stimulation in Humans," Visual Neuroscience, 2015, vol. 56, No. 8, pp. 4680-4688.

Fisher, et al., "Photic- and Pattern-induced Seizures: A Review for the Epilepsy Foundation of America Working Group," Epilepsia, Sep. 1, 2005, vol. 46, No. 9, pp. 1426-1441.

Kasteleijn-Nolst Trenite, et al., "Methodology of photic stimulation revisited: Updated European algorithm for visual stimulation in the EEG laboratory," Epilepsia, Nov. 16, 2011, vol. 53, No. 1, pp. 16-24.

Topalkara, et al., "Effects of flash frequency and repetition of intermittent photic stimulation on photoparoxysmal responses," Seizure, Jun. 1, 1998, vol. 7, No. 3, pp. 249-255.

Siniatchkin, et al., "Spreading photoparoxysmal EEG response is associated with an abnormal cortical excitability pattern," Brain, Nov. 21, 2006, vol. 130, No. 1, pp. 78-87.

Schielke, et al., "Reduced stead-state following responses in primary visual cortex in an animal model of schizophrenia," Journal of Vision, Sep. 2016, vol. 16, No. 12, p. 1227.

Humayun, et al., "Pattern electrical stimulation of the human retina," Vision Research, Feb. 11, 1999, vol. 39, No. 15, pp. 2569-2576.

Fedotchev, et al., "Stability of resonance EEG reactions to flickering light in humans," International Journal of Psychophysiology, Sep. 1, 1990, vol. 9, No. 2, pp. 189-193.

Rager, et al., "The response of cat visual cortex to flicker stimuli of variable frequency," European Journal of Neuroscience, May 1, 1998, vol. 15, No. 5, pp. 1856-1877.

Vieria, Mario Antonio Moraes, "Efeitos de um program conjugado da metodologia de luz e som e pratica motriz complexa em funcoes de memoria em individuos portadores da doenca de Alzheimer: relacoes com hemisfericidade," Dissertacao de Mestrado—Rio de Janeiro: Universidade Castelo Branco, Sep. 12, 2008, pp. 1-146.

* cited by examiner

APPARATUS FOR NEURAL STIMULATION AND METHOD OF USE

FIELD OF THE INVENTION

The present invention generally relates to the field of neural stimulation. In particular, the present invention is directed to an apparatus for neural stimulation.

BACKGROUND

A key duration milestone to maximizing efficacy of various stimuli to the brain to reduce amyloid beta plaques is exposure of gamma entrainment over an extended period of time. However, this can be difficult for a patient to allot a large amount of time daily to be exposed to the stimuli. In addition, some patients may require co-administration of multiple forms of stimuli such as auditory stimuli and visual stimuli. Current systems do not provide for co-administration of various stimuli to the brain. In addition, current systems do not allow for stimuli to be emitted only when a user is asleep.

SUMMARY OF THE DISCLOSURE

In an aspect an apparatus for neural stimulation is described. The apparatus includes a head device configured to be worn on a head of a user. The head device includes at least one light-emitting device configured to provide photic entertainment to the user and at least one control module electrically connected to the at least one light-emitting device and configured to receive one or more stimulatory commands, wherein the at least one control module is configured to operate the at least one light-emitting device as a function of the one or more stimulatory commands. The apparatus further includes at least one computing device communicatively connected to the head device, the computing device having a processor and a memory communicatively connected to the processor. The memory contains instructions configuring the processor to receive user data, wherein the user data includes information relating to a neural state of a user, generate the one or more stimulatory commands as a function of the user data including determining the neural state of the user, and transmit one or more stimulatory commands to the head device.

In another aspect, a method for neural stimulation is described. The method includes obtaining a head device configured to be worn on a head of a user, the head device including a light-emitting device configured to provide photic entertainment to the user and a control module. The method further includes receiving, by a computing device communicatively connected to the head device, user data wherein the user data includes information relating to an neural state of a user, generating, by the computing device, one or more stimulatory commands including determining the neural state of the user, transmitting, by the computing device, the one or more stimulatory commands to the head device modifying, at the control module, a light from the at least the light-emitting device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for Neural simulation. In some embodiments, aspects of tis disclosure may include light-emitting devices, audio-output devices, transcranial focused ultrasound devices, and the like.

Aspects of the present disclosure can be used to provide neural stimulation to a user. Aspects of this disclosure can also be used to provide co-administration of one or more neural stimulation techniques. Aspects of this disclosure can further be used to provide neural stimulation to a user while they are asleep. Exemplary embodiments illustrating aspects of the present disclosure are described below in the context of several specific examples.

Figure 1:
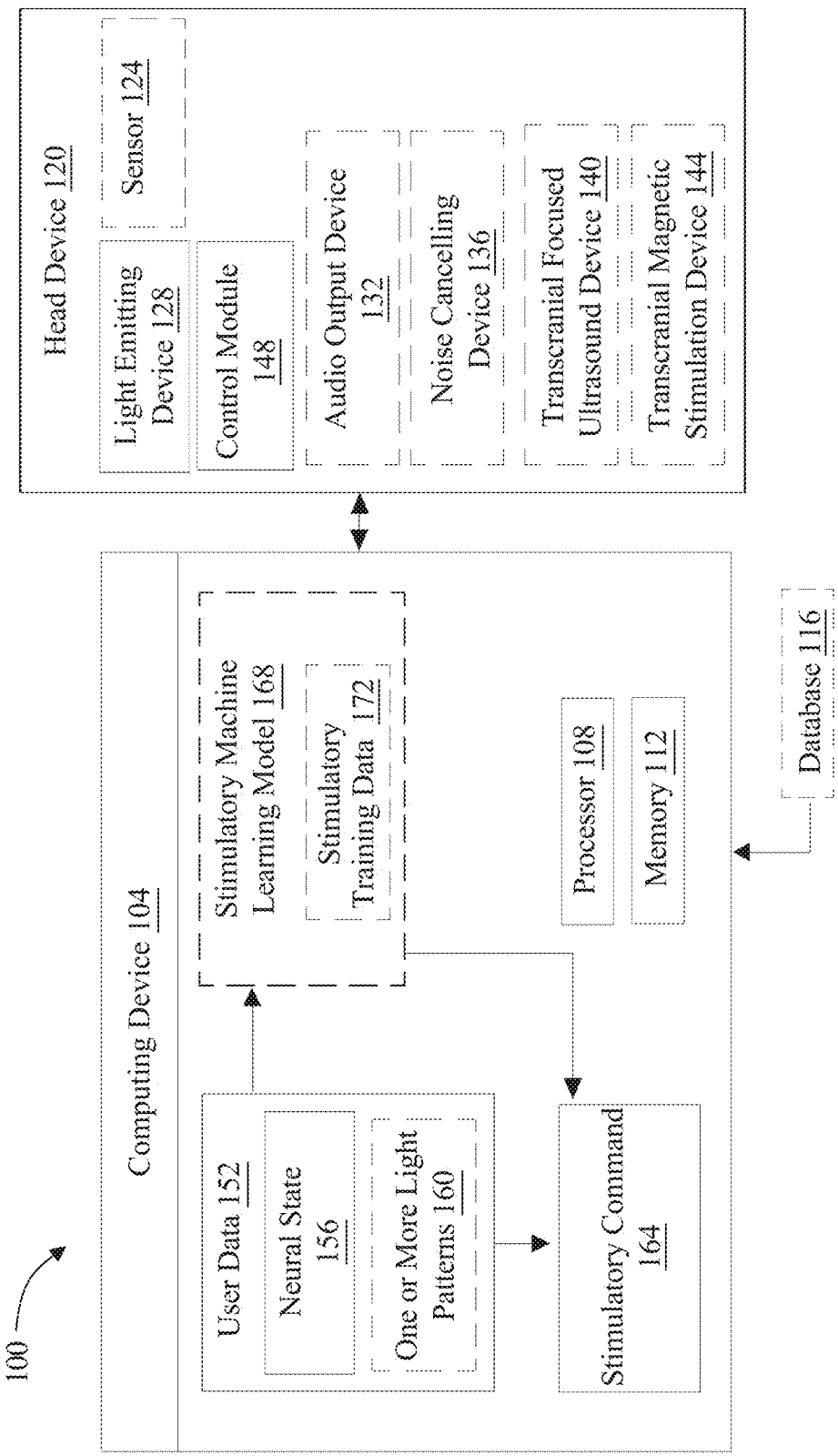
FIG. 1 is a block diagram of an exemplary embodiment of an apparatus for neural stimulation.

Referring now to FIG. 1, an exemplary embodiment of an apparatus 100 for neural stimulation is described. For the purposes of this disclosure "neural stimulation" is modulation of brain activity using invasive or noninvasive measures. In some cases, neural stimulation may include the use of electrodes, light, magnetic fields, ultrasounds, and the like. In some cases, neural stimulation may provide for treatment of neurological disorders such as Parkinson, epilepsy, agfe related macular degeneration and other neurological disabilities. In some cases, neural stimulation may be used for the treatment of one or more neurological disorders as described below. In some cases, neural stimulation may be used to improve the sleep of a user. In some cases, one or more stimuli as described in this disclosure may be used to improve sleep duration and quality, thereby treating another symptom of neurological disorders. The terms "neural oscillation" and "neural stimulation" are meant to include several modalities that can cause repetitive neural activity in the central nervous system of humans or animals, in individual, or interactions of, neurons. Neural oscillations are an example of an indicator of electrical neural activity measured invasively via extracellular recordings as local field potentials (LFP), or non-invasively by magnetoencephalogram (MEG) or electroencephalogram (EEG). Neural oscillations are rhythmic fluctuations generated by the activity of local neuron populations or neuron assemblies across brain areas. Electrical activity in the brain known as "gamma"

brainwaves help connect and process information throughout the brain. Gamma waves can be reduced in frequency, intensity and rhythm in neurodegenerative diseases and conditions of cognitive decline. Gamma wave stimulation, also known as "entrainment," may be beneficial to brain health and function, and directly manipulated microglia. Gamma oscillation is the synchronization with a frequency of 30-90 Hz of neural oscillations. The interaction between homeostatic microglia and synapses increases neuronal activity and contributes to the synchronized firing of local neuronal populations and may therefore treat various conditions.

With continued reference to FIG. 1, apparatus 100 includes a computing device 104. Apparatus 100 includes a processor 108. Processor 108 may include, without limitation, any processor 108 described in this disclosure. Processor 108 may be included in and/or consistent with computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, apparatus 100 includes a memory 112 communicatively connected to processor 108. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, apparatus 100 may include a database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, apparatus 100 includes a head device 120. "Head device" for the purposes of this disclosure is a device configured to provide treatment for one or more neurological dysfunctions or disorders. For example, head device 120 may include one or more components, wherein the one or more components may provide neural stimulation to a user. "User" for the purposes of this disclosure is an individual operating apparatus 100. User may include an individual looking to treat a neurological condition. In some cases, head device 120 may include a housing wherein the housing is configured to fit onto a portion of a user's head. For example, head device 120 may include a housing in the shape of glasses or goggles, wherein a user may wear head device 120 is similar to a pair of glasses or goggles. In some cases, the glasses or goggles may cover or at least partially cover a user's field of vision. In some cases, head device 120 may include a housing in the shape of a helmet wherein a user may place head device 120 on top of a portion of the user's head. In some cases, head device 120 may be configured to be worn on the head of a user. In some cases, head device 120 may be worn on one or more portions of a user's head, such as a forehead, the frontal region, the occipital region, the auricular region, the mental region, the hair line, the parietal region, the parietal eminence, the orbital region, the temporal region and the like. In some cases, head device 120 may be positioned on any portion of a user's head, wherein neural stimulation may properly be administered. In some cases, head device 120 may be configured to partially obstruct a view of a user, wherein a user may use head device 120 as a sleep aid and 'mask' surrounding light. In some instances, head device 120 may be optogenic including producing and/or emitting light. In some cases, head device 120 may include a power source such as one or more batteries and/or a plug to be connected to a power source. In some cases, power source may be used to power one or more devices through electrical energy as described below.

With continued reference to FIG. 1, head device 120 may include a sensor 124. As used in this disclosure, a "sensor" is a device that is configured to detect an input and/or a phenomenon and transmit information related to the detection. Sensor 124 may be configured to receive one or more elements within user data 152 as described below. In some cases, sensor 124 may be configured to receive information relating to the neural activity of a user. For example, sensor 124 may receive information indicating if a user is currently awake or asleep. In some cases, sensor 124 may include a heart rate sensor 124 wherein sensor 124 may be configured to receive a heart rate of a user and determine a conscious state of the user such as whether the user is awake or a sleep. In some cases, sensor 124 may include electrocardiogram (ECG) monitor wherein sensor 124 may be configured to receive a user's heart and determine if a user is awake or asleep. In some cases, sensor 124 may include one or more electroencephalography (EEG) monitors wherein sensor 124 may be configured to receive electrical activity of the user's brain and make one or more determinations about the sleep activity and the level of sleep associated with the user. In some cases, sensor 124 may include one or more respiratory sensors, and the like. In some cases, sensor 124 may include any sensor 124 that may be configured to make one or more determinations about a user's state of consciousness. This may include, but is not limited to, accelerometers, gyroscopes, temperature sensors, pressure sensors, light sensors, pulse oximeters, and the like. In some cases, data received from sensor 124 may be transmitted to computing device. Computing device may receive information from sensor 124 and make one or more determinations about a user as a function of the data received from the sensor 124.

With continued reference to FIG. 1, sensor 124 may include a functional near-infrared spectroscopy sensor (fNIRS). "fNIRS" for the purposes of this disclosure is a sensor configured to measured brain activity by detecting changes in blood oxygenation and blood volume in the frame. fNIRS works by shining near-infrared light (typically between 650 and 900 nanometers, which can penetrate biological tissues) onto the scalp. Some of this light is absorbed by the brain tissue and blood, while some is scattered and reflected back to the surface where it can be detected by one or more sensors 124. The reflected light that returns to the detectors has traveled through several centimeters of tissue, including the outer layers of the brain (the cortex), and carries information about changes in the concentrations of oxygenated and deoxygenated hemoglobin. By analyzing these changes in light absorption, fNIRS may provide a measure of brain activity and thus grade of consciousness of a user. In some cases, sensor 124 may be positioned close to a user's head in order to receive information relating to brain activity. In some cases, sensor 124 may be configured to receive any information relating to a user's neural activity wherein computing device 104 may make determinations as a function of the neural activity. In some cases, sensor 124 may be configured to receive hemoglobin-concentration in the brain based on optical intensity measurements. In some cases, sensor 124 may be configured to measure and receive voltage fluctuations associated with a user's neural activity. In some cases, sensor 124 may be configured to receive information relating to brain activity wherein computing device 104 may make determinations about a user's neural activity.

Still referring to FIG. 1, in some embodiments, apparatus 100 and/or sensor 124 may additionally include at least a camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor 124. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image.

Still referring to FIG. 1, sensor 124 may include a motion sensor 124. A "motion sensor", for the purposes of this disclosure, refers to a device or component configured to detect physical movement of an object such as a user. One of ordinary skill in the art would appreciate, after reviewing the entirety of this disclosure, that motion may include a plurality of types including but not limited to: spinning, rotating, oscillating, gyrating, jumping, sliding, reciprocating, or the like. Sensor 124 may include gyroscope, accelerometer, torque sensor, magnetometer, inertial measurement unit (IMU), pressure sensor, force sensor, proximity sensor, displacement sensor, vibration sensor, among others.

With continued reference to FIG. 1, sensor 124 may be configured to transmit a sensor output signal representative of sensed information. As used in this disclosure, a "sensor signal" is a representation of a sensed information that sensor 124 may generate. A sensor signal may include any signal form described in this disclosure, for example digital, analog, optical, electrical, fluidic, and the like. In some cases, a sensor, a circuit, and/or a controller may perform one or more signal processing steps on a signal. For instance, sensor, circuit, and/or controller may analyze, modify, and/or synthesize a signal in order to improve the signal, for instance by improving transmission, storage efficiency, or signal to noise ratio.

With continued reference to FIG. 1, exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor 108 (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

Still referring to FIG. 1, in some embodiments, apparatus 100 may include a machine vision system that includes at least a camera. A machine vision system may use images from at least a camera, to make a determination about a scene, space, and/or object. For example, in some cases a machine vision system may be used for world modeling or registration of objects within a space. In some cases, machine vision system may be used to determine if a user is awake or asleep. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ϕ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

With continued reference to FIG. 1, head device 120 includes a light-emitting device 128 configured to provide photic entrainment to a user. "Photic entrainment," for the purposes of this disclosure, is the realignment of the circadian system in response to light emission. Photic entrainment may be used to realign a user's sleep cycle. In some cases, photic entrainment may be used in the treatment of various neurological disorders such as Parkinson's disease, Alzheimer's disease, dementia, age related macular degeneration, and the like. In some cases, exposure to light or photic entrainment may be used to increase gamma brainwaves and lead to a clearing of beta amyloid plagues in the brain, a key abnormality in Alzheimer's disease. This may be so by encouraging protective cells to phagocytize the harmful proteins that accumulate in the brain. In some cases, photic entrainment may aid in the improvement of cognitive functions of patients with Alzheimer's and dementia which may help avoid symptoms of cognitive decline. "Light-emitting device" for the purposes of this disclosure is a device capable of emitting one or more light waves. In some cases, the light-emitting device 128 may include light-emitting diodes, organic light-emitting diodes, fluorescent lamps, lases and the like. In some cases, the light emitted from light-emitting device 128 may vary in wavelength. For example, the light may include a violet light ranging between 400 and 420 nanometers (nm). In some cases, the light may include a violet light, indigo light (420-440 nm), blue light (440-490 nm), green light (490-570 nm), yellow light (570-585 nm), orange light (585-620 nm), red light (620-720 nm), infrared light (720 nm-1 mm) and the like. In some cases, light-emitting device 128 may emit a white light, wherein the white light is a combination of all colors in the color spectrum. In some cases, light-emitting device 128 may emit any visible or non-visible light. In some cases, light-emitting device 128 may include a light frequency. "Light frequency" for the purposes of this disclosure is the number of complete oscillations of waves that pass through any given point over a particular unit of time. Light frequency is typically measured in 'Hz' of 'hertz' wherein a given number of hertz denotes the number of cycles per second. In some cases, Light-emitting device 128 may emit light at a given frequency between 30 and 90 Hz. In some cases, light-emitting device 128 may emit light between 38 and 44 Hz. In some cases, light-emitting device 128 may emit light at 40 Hz. In some cases, light-emitting device 128 may emit light at any given frequency suitable for photic entrainment. In some cases, a light-emitting from light-emitting device 128 may vary in intensity. The intensity may be measured in lumens per square meter or 'lux' wherein an increase in intensity may increase the lumens per square meter and a decrease may decrease the Lux. In some cases, intensity of light-emitting device 128 may vary based on a user's surroundings. For example, if a user is in a dimly lit area and correspondingly their pupils are constricted, light-emitting device 128 may choose a lower intensity. However, in situations where a user is in a well-lit area and the users' pupils are dilated, the intensity may be increased in order to compensate for the surrounding light. In some cases, intensity may differ based on a user neurological dysfunction or based on a user's preferences.

With continued reference to FIG. 1, light-emitting device 128 may direct a selected light pattern or frequency toward the retinal cones of the eye of a user from directly in front of the eye, thereby penetrating the eyelid. In some cases, light emitting device 128 may direct a selected light pattern or frequency toward the retinal cones at an angle, wherein light emitting device may be situated near a user's eye such as proximal to a user head. This may allow for photic entrainment even when a user may be asleep, or when their eyes are simply closed. In some cases, the light emitted from light-emitting device 128 may be referred to as "photic entrainment stimuli". In another aspect, photic entrainment stimuli may be 'masked' by their inclusion in other light patterns 160, intensities, powers, wavelengths, frequencies, and durations, thereby making the strobing effect either wholly or partly imperceivable to the user. In some aspects, the apparatus 100 may be used while the user is awake and with an alternate and/or a second light emitting device situated proximal to the user's eye versus in front. In some cases, light emitting device 18 may be configured for low level light therapy. "Low level light therapy" sometimes known as "photo modulation" or "photo biomodulation" is a therapy using low intensity light to penetrate tissue and promote healing. In some cases, low level light therapy may be used to treat acute or chronic pain. In some cases, low level light therapy may further be used to reduce inflammation, help with various injuries and the like. In some cases, low level light therapy may include red and near infrared light (600-100 nm). In some cases, low level light therapy may be used to treat one or more skin conditions. In some cases, low level light therapy may be used to promote soft tissue healing. In some cases, low level light therapy may reduce oxidative stress and increase adenosine triphosphate production (ATP). In some cases, low level light therapy may improve cellular metabolism, reduce inflammation, increase blood flow and the like. In some cases, low level light therapy may be used to treat one or more neurological disorders and/or ne or more symptoms associated with neurological disorders. In some cases, light emitting device 128 may be used for optogenetics. "Optogenetics" for the purposes of this disclosure is a process in which a light may be configured to control the activity of one or more neurons in a user's brain. This may be done through the introduction of light sensitive ion channels in specific cells wherein a light may allow for control of the light sensitive light through the emission of light. In some cases, optogenetics may be used to treat one or more neurological disorders. In some cases, optogenetics may be used to improve motor control, neural activity and the like.

With continued reference to FIG. 1, head device 120 may include an audio output device 132. An "audio output device" for the purposes of this disclosure is a device configured to convert electrical signals into auditory sound waves. In some cases, the audio output device 132 may receive one or more electrical audio signals from computing device. In some cases, computing device may generate one or more electrical audio signals and transmit the signals to audio output device 132. In some cases, audio output device 132 may include a speaker, headphones, earphones and the like. In some cases, head device 120 may be communicatively connected to audio output device 132. In some cases, head device 120 may be connected to audio output device 132 through a Bluetooth connection. In some cases audio output device 132 may emit sounds at one or more frequencies. In some case, audio output device 132 may be configured to module neural activity and provide neural stimulation. In some cases, audio output device 132 may direct a selected sound vibration toward a user's ear and/or conductivity into the skull and/or cochlear cells within the ear. In some cases, audio output device 132 may be configured to direct sounds into a skull using bone conduction. "Bone conduction" for the purposes of this disclosure refers to a process in which vibrations are transmitted to the bones of a person's skull rather than through the ears. In some cases, bone conduction may provide for transmission of sounds to a user's skull in individuals who may have conductive hearing less. In bone conduction, a device is situated in close contact to a user's skull wherein vibrations are sent to the bones within the user's skull. The vibrations are then sent to the inner ear through the vibrations. In some cases, audio output device 132 may generate binaural beats. "Binaural beats" for the purposes of this disclosure are tones emitted at slightly differing frequencies that are configured to cause an individual's brain to create auditory illusions after receipt of the tones. In some cases, binaural beats may be used to modify brain function. In some cases, audio output device 132 may generate binaural beats at differing frequencies depending on the particular needs of a user. For example, audio output device 132 may emit sound at 1-4 Hz to aid a user in deep sleep, for healing and pain relief for anti-again properties and the like. In some cases, audio output device 132 may emit one or more sounds at a range of 1-100 hz. In some cases, the audio output device 132 may emit sounds form between 1-4 Hz, 4-8 Hz, 8-14 Hz, 14-30 Hz, and/or 30-100 Hz. In some cases sounds emitted by audio output device 132 may be used to treat cognitive decline in a user through the emission of sounds at varying frequencies. In some cases, audio output device 132 may emit binaural beats along with other auditory signals. For example, audio output device 132 may be configured to output music, audio recordings and the like along with varying sounds configured for neural stimulation. In an embodiment, the sounds configured for neural stimulation may be 'masked' by other sounds emitted by audio-output device. In some cases, audio-output device may emit other sounds in order to mask varying auditory sounds from the user. In some cases, sounds emitted from audio output device 132 may be referred to as auditory stimuli wherein the auditory stimuli may be configured to provide neural stimulation. In some cases, auditory stimuli may be 'masked' by their inclusion with other sounds, patterns, intensities, powers, wavelengths, frequencies and durations, for example, music, white noise, and/or binaural beats, thereby making them either wholly or partly imperceivable to the user. In this aspect, the apparatus 100 may be used to aid in falling asleep.

With continued reference to FIG. 1, head device 120 may include a noise-cancelling device 136. A "noise-cancelling device" for the purposes of this disclosure is a device configured to reduce background noise associated with a user. For example, noise-cancelling device 136 may be used to mask background noises associated with traffic nearby, people talking near a user, and other sounds that may contribute to unwanted background noise. In some cases, noise cancelling device 136 may include an audio input configured to receive background noises and an audio output configured to emit one or more sounds. In some cases, noise cancelling device may include sensor 124, wherein sensor is configured to receive audio input. In some cases, noise cancelling device 136 may further include audio-output device 132, wherein audio output device is configured output one or more sounds. In some cases, noise cancelling device may include separate components from sensor 124 and audio-output device 132. In some cases, noise-cancelling device 136 may include a microphone configured to receive background noise associated with a user. As used in this disclosure, a "microphone" is any transducer configured to transduce pressure change phenomenon to a signal, for instance a signal representative of a parameter associated with the phenomenon. Microphone, according to some embodiments, may include a transducer configured to convert sound into electrical signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). Microphone may include any microphone for transducing pressure changes, as described above; therefore, microphone may include any variety of microphone, including any of condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone. In some cases, sensor 124 may include a microphone. In some cases, microphone may be configured to receive an audio signal. An "audio signal," as used in this disclosure, is a representation of sound. In some cases, an audio signal may include an analog electrical signal of time-varying electrical potential. In some embodiments, an audio signal may be communicated (e.g., transmitted and/or received) by way of an electrically transmissive path (e.g., conductive wire), for instance an audio signal path. Alternatively or additionally, audio signal may include a digital signal of time-varying digital numbers. In some cases, a digital audio signal may be communicated (e.g., transmitted and/or received) by way of any optical fiber, at least an electrically transmissive path, and the like. In some cases, a line code and/or a communication protocol may be used to aid in communication of a digital audio signal. Exemplary digital audio transports include, without limitation, Alesis Digital Audio Tape (ADAT), Tascam Digital Interface (TDIF), Toshiba Link (TOSLINK), Sony/Philips Digital Interface (S/PDIF), Audio Engineering Society standard 3 (AES3), Multichannel Audio Digital Interface (MADI), Musical Instrument Digital Interface (MIDI), audio over Ethernet, and audio over IP. Audio signals may represent frequencies within an audible range corresponding to ordinary limits of human hearing, for example substantially between about 20 and about 20,000 Hz. According to some embodiments, an audio signal may include one or more parameters, such as without limitation bandwidth, nominal level, power level (e.g., in decibels), and potential level (e.g., in volts). In some cases, the relationship between power and potential for an audio signal may be related to an impedance of a signal path of the audio signal. In some cases, a signal path may single-ended or balanced.

With continued reference to FIG. 1, microphone may be configured to transduce an environmental noise to an environmental noise signal. In some cases, environmental noise may include any background noise, ambient noise, aural noise, such as noise heard by a user's ear, and the like. Additionally or alternatively, in some embodiments, environmental noise may include any noise present in an environment, such as without limitation an environment surrounding, proximal to, or of interest/disinterest to a user. Environmental noise may, in some cases, include substantially continuous noises, such as a drone of an engine. Alternatively or additionally, in some cases, environmental noise may include substantially non-continuous noises, such as spoken communication or a backfire of an engine. Environmental noise signal may include any type of signal, for instance types of signals described in this disclosure. For instance, an environmental noise signal may include a digital signal or an analog signal.

With continued reference to FIG. 1, noise-cancelling device 136 may be configured to receive an environmental signal and generate an inverted wavelength of the environmental noise to cancel out the resulting environmental noise. "Inverted wavelength" for the purposes of this disclosure is a noise wave having an inverted wavelength in comparison to the environmental noise signal. For example, in instance wherein environmental noise signal contains a high noise wave interview wavelength may contain a low noise wave. Noise-cancelling device 136 may be communicatively connected to computing device 104 wherein computing device may be configured to receive environmental signal and generate an inverted wavelength to be used to cancel out the environmental noise. Inverted wavelength may be generated by inverting environmental noise signal by multiplying environmental noise signal by −1. In some cases, noise-cancelling device 136 may be configured to reduce background noise of a user, such that audio output device 132 may generate sounds that provide neural stimulation to a user. In some cases, audio output device 132 may be configured to generate both noise cancelling waves and binaural beats wherein the noise cancelling waves may be configured to cancel out ambient noise while audio output device 132 still generates sounds for the user. In some cases, audio output device 132 may generate multiple sound signals in sync such that ambient noise may be cancelled out while audio configured to neural stimulation is still provided.

With continued reference to FIG. 1, head device 120 may include a transcranial focused ultrasound device 140 (TFUD). A "transcranial focused ultrasound device" or "transcranial focused ultrasound stimulation" (TFUS), for the purposes of this disclosure, is a device configured to provide neural stimulation to a user through the use of low intensity sound waves. TFUD 140 may be configured to emit ultrasound waves non-invasively to various regions of a user's brain. In some cases, low intensity ultrasound waves may be focused onto various areas of a user's brain. In some cases, ultrasound waves may be configured to allow for penetration of areas in the brain that may not be accessed without invasive procedures. In some cases, TFUD 140 may be configured to treat conditions such as Parkinson's essential tremor and the like. In some cases, TFUD 140 may be configured output pulses or 'bursts" wherein each pulse may vary based on intensity frequency and duration. As opposed to high intensity focused ultrasound, short bursts (in contrast to a continuous pulse) allow for neural stimulation and not tissue ablation in the brain. In some cases, the burst may vary in frequency from between 0.25 MHz to 2.5 Mhz. In some cases, each burst may contain a maximum frequency of 10 Mhz and a minimum frequency of 0.1 Mhz. In some cases, the intensity of each burst may vary from 10.0 mW/Cm^2 to 60.0 mW/Cm^2. In some cases, TFUD 140 may have a duration varying from 0.2 ms to 1000 ms. In some cases, TFUD 140 may have a duration of 0.5 ms. In some cases, TFUD 140 may have a duration of 1 ms. In some cases, the pulse intensity, duration and frequency may vary based on the needs of a user. in some cases, TFUD 140 may include an ultrasound transducer, wherein the transducer is configured to generate the ultrasound waves. The transducer may convert electrical signals into sound waves. The electrical signals may be received from computing device as described in this disclosure. In some cases, TFUD 140 may further include an ultrasonic lens configured to focus one or more sound waves to a particular point. The lens may be configured to pinpoint particular areas in a user's brain in which the sound waves may target and provide neural stimulation. In some cases, TFUD 140 may include a control unit or may be communicative connected to a control unit wherein the intensity, duration and frequency of the waves may be controlled and/or modified. In some cases, TFUD 140 may be configured to open a blood-brain barrier of a user. The blood-brain barrier is a system that maintains homeostasis on the brain. The blood brain barrier is configured to prevent infectious agents from entering the brain. However, the blood-brain barrier may further prevent useful medications from reaching the brain. In some cases, TFUD 140 may open the blood-brain barrier and allow for medications to enter a user's brain and/or surrounding area. In some cases, TFUD 140 may be configured to facilitate the delivery of one or more medications used for neurological disorders.

With continued reference to FIG. 1, head device 120 may include a transcranial magnetic stimulation device 144. A "transcranial magnetic stimulation (TMS) device" 144 for the purposes of this disclosure is a device configured to modulate brain activity using magnetic field to stimulate nerve cells in the brain. In some cases, TMS device 144 may provide for treatment of neurological disorders such as obsessive-compulsive disorder, depression, addiction, age related macular degeneration, and the like. In some cases, TMS device 144 may include a magnetic coil, wherein the magnetic coil is configured to be placed on the scalp of a user's head and provide magnetic pulses to various regions of a user's brain. In some cases, TMS device 144 may emit a single pulse or a series of pulses wherein the pulses may vary in frequency and duration. In some cases, the pulses may vary in frequency below 1 Hz, wherein the pulses may be configured to inhibit cortical firing whereas as frequency of greater than 1 Hz may be configured to increase cortical firing. "Cortical firing" for the purposes of this disclosure refers to the frequency in which action potentials are generated. Action potentials are responsible for the communication between neurons in the brain. An change in the frequency of action potentials may allow for the treatment of neurological dysfunctions that may be caused by an imbalance of action potential frequency. In some cases, TMS device 144 may include a magnetic coil wherein a current is passed through the coil to generate a magnetic field for neural stimulation. In some cases, TMS device 144 may further include a capacitor configured to provide a current to the coil. In some cases, a capacitor may be used to ensure that the magnetic coil receives the proper electrical energy in order to emit a magnetic field. In some cases, TMS device 144 may include a power source such as a battery or a power unit configured to power the magnetic coil. In some cases, TMS device 144 may be connected to a control unit, wherein the control unit is configured to provide energy to the TMS device 144 and to control the pulses and frequency associated with the TMS device 144.

With continued reference to FIG. 1, head device may include a signaling device configured to directs a selected scent, light or vibrational pattern nasally toward the olfactory organs. In some cases, the signaling device may contain one or more scents, wherein the scents are configured to be released and directed toward the olfactory organs of a user. The scents may include, but is not limited to, lavender, peppermint, eucalyptus, lemon, jasmine, coffee, chamomile, sage, thyme, rose, geranium and the like. In some cases, the signaling device may be configured to direct one or more scents to the olfactory organs to provide neural stimulation. In some cases, signaling device may be configured to generate one or more scents using brain stimulation. In some cases, signaling device may be configured to simulate one or more smells within a user's brain using electrical stimulation.

With continued reference to FIG. 1, head device 120 may further include a transcranial direct current stimulation device (tDCS). "Transcranial direct current stimulation device" for the purposes of this disclosure is a device configured to provide neural stimulation in the form of electrical stimuli to the brain. In some cases, tDCs may contain one or more electrodes configured to provide electrical currents to a user's brain. In some cases, one or more electrodes may be placed in varying regions on head device 120 to provide electrical stimuli to varying regions of a user's brain. In some cases, tDCS may be placed on two different regions of a user's brain. In some cases, tDCS may tDCS may be configured to modify neural behavior such as excitability and activity levels, accelerate earning and boost task performance. In some cases, tDCS may be used to treat or improve cognitive functions associated with one or more neurological disorders. In some cases, head device 120 may include transcranial alternating current stimulation device (tACS). In contrast to tDCS, tACS provides neural stimulation to the brain in the form of an alternating current rather than a direct current. In some cases the alternating current may contain a particular frequency used to provide neural stimulation to varying regions of a user's brain. In some cases an alternating current may provide for manipulation and entrainment of neural oscillations in the brain region. In some cases, an alternating current can interact with ongoing neural activity and potentially influence brain function.

With continued reference to FIG. 1, head device 120 may include one or more modular components. "A modular component" for the purposes of this disclosure is a device that may be removably attached to head device 128. In some cases, modular component may include light-emitting device 128, audio output device 148, noise cancelling device 136, TFUD 140, TMS device 144 and any other device as described in this disclosure that is configured to provide neural stimulation and/or stimuli. In some cases, head device 120 may include one or more modular components wherein user may select only the modular components that are necessary at the moment. In some cases, modular components may be used to replace one or more devices with one or more devices of differing intensities. For example, light emitting device 128 may be removed from head device 128 and replaced with a light emitting device of a differing frequency or intensity when necessary. In some cases, modular component may allow for the removal of one or more neural stimulation devices as described in this disclosure. In some cases, modular components may allow for the combination of various neural stimulation devices as described in this disclosure. In some cases, modular component may allow for the attachment of one or more similar devices. For example a user may wish to attach two TMS devices 144 to head device 128. In some cases, modular components may allow for the configuration of head device 128 based on a particular neurological disorder. For example, a patient with Alzheimer's may seek to have a particular set of modular components whereas a patient with dementia may seek to have a differing configuration of modular components. In some cases, head device 128 may include one or more electrical ports that provide electrical power to one or more modular components. In some cases, head device 128 may contain one or more mating mechanisms, wherein the mating mechanisms are configured to secure the modular components to head device 128.

With continued reference to FIG. 1, head device 120 includes a control module 148. "Control module" for the purposes of this disclosure is a device configured to manage other mechanical devices. For example, control module 148 may be used to control the emission of light from light-emitting device 128. In some cases, control module 148 may be communicatively connected to any device described within this disclosure which is configured to provide neural stimulation or photic entrainment. In some cases, control module 148 may be electrically connected to one or more devices (e.g. light-emitting device 128, audio output device 132, TFUD 140, TMS device 144 and the like) as described in this disclosure. In some cases, control module 148 may be electrically connected to at least light-emitting device 128 and configured to receive commands (as described below), wherein control module 148 is configured to operate at least light-emitting device 128 as a function of the commands. In some cases, control module 148 may be configured to modify a light emitted from light-emitting device 128 by modifying the intensity or frequency of light-emitting device 128. In some cases, control module 148 may be configured to receive one or more commands and convert them commands into electrical signals suitable for controlling one or more device. For example, control module 148 may receive a command to emit a sound from audio output device 132 wherein control module 148 may convert the command into an electrical signal which can be used to output audio from audio output device 132. In some cases, control module 148 may be configured to receive a command, process the command using a processing unit such as processor 108, and convert the command into an electrical signal. In some cases, the electrical signal may include an analog signal wherein control module 148 may convert the digital signal into an analog signal for one or more devices. In some cases, control module 148 may be configured to operate mechanical components associated with one or more devices as described in this disclosure. This may include but is not limited to, motors, actuators, solenoids, and any other components that may be used to convert an electrical signal into mechanical energy. In some cases, control may control one or more electrical audio signals, such as by, increasing or decreasing a volume associated with the signals, or determining when a particular electrical audio signal should be sent. In some cases, control module 148 may be configured to control noise-cancelling device 136, such as by controlling the amount of environmental noise that may pass through to a user. In some cases, cases control module 148 may control the pulse duration, intensity, and frequency of TFUD 140 wherein control modules 148 may increase or decrease intensities, frequencies, and durations of each pulse associated with TFUD 140. In some cases, control module 148 may be configured to modify a frequency and pulse duration associated with TMS device 144. In some cases, control module 148 may include a computing device as described in this disclosure wherein control module 148 is configured to transmit commands or electrical signals to one or more devices. In some cases, control module 148 may control the settings (e.g. intensity, pulse, duration, frequency etc.) for each device by varying the voltages, currents, the pulse width modulation and the like. In some cases, control module 148 may be configured to modify or alter the frequency, pulse duration and intensity of TFUD 140 and/or TMS device 144. In some cases, control module 148 may be configured to alter the frequency, lumens and the like with light-emitting device 128. In some cases, control module 148 may be configured to alter an output of any device as described in this disclosure configured for neural stimulation and/or photic entrainment. In some cases, control module 148 may be consistent with computing device and may be configured to generate and transmit commands to one or more devices.

With continued reference to FIG. 1, processor 108 is configured to receive user data 152. "User data" for the purposes of this disclosure is data pertaining to a user seeking neural stimulation. User data 152 may include basic background information such as the age, gender, height, weight, and the like of a user. In some cases, user data 152 may further include a particular neurological disorder that a user is suffering from. The neurological disorder may include but is not limited to dystonia, epilepsy, essential tremor, Parkinson's disease, depression, obsessive compulsive disorder and the like. The neurological disorder may include any disorder that may be treated with neurological stimulation. User data 152 may further include a user's sleep schedule (e.g. typical time the user goes to sleep, typical time the user wakes up, average number of hours slept a night, and the like). In some cases, user data 152 may include user the severity of a particular neurological disorder. In some cases, each neurological disorder may include a rating wherein a particular rating may signify the severity of the disorder. For example, user data 152 associated with a user with Parkinson's disease may include a rating of 1-5 wherein a 1 may signify an early onset of Parkinson's disease and rating of 5 may signify severe symptoms associated with the disease. In some cases, user data 152 may include user preferences. "User preferences" for the purposes of this disclosure is one or more settings or commands associated with a particular device associated with neural stimulation. For example, user preferences may include a command to activate a light for neural stimulation, a preferred intensity of the light, a particular time frame for emitting the light and the like. In some cases user preferences may include one or more settings and/or one or more commands associated with a neural stimulation device. In some cases, user day may include medical data (e.g. medical history, medications taken, treatments given, allergies, dosage of treatments, future medical visits, previous medical visits, progression of a particular neurological disorder and the like.). In some cases, user data 152 may include any data necessary to make one or more determinations about a particular neurological disorder. This may include, but is not limited to, determinations relating to settings associated with neurological stimulation devices, determinations about medications associated with neurological disorders and the like.

With continued reference to FIG. 1, user data 152 includes information relating to a neural state 156 of a user. "Neural state" for the purposes of this disclosure is information regarding the neural activity of a user. For example, neural state 156 may include neural activity indicating that a user may be awake, or asleep (or unconscious). Neural state 156 may further include a user's neural activity in response to one or more stimulatory responses. For example, neural state 156 may include a user's neural activity when light is emitted at the user. In some cases, neural state 156 may be used to track changes in brain activity over time, helping to evaluate the long-term efficacy of the one or more neural stimulation devices described in this disclosure. This may be valuable in determining the treatment's overall success and whether modifications are needed. In some cases, neural state 156 may be used to help monitor a user's neurophysiological responses to light therapy. This information may be used to adjust treatment parameters (like timing, intensity, and wavelength of light) to optimize therapeutic effects and minimize side effects. In some cases, neural state 156 may be used to determine whether a user is awake or asleep. Ins some cases, neural state 156 may include any information that may be used to make a determination on whether is awake or asleep. For example, neural state 156 may include heart rate, body temperature, data relating to brain functions, data relating to the movements of a user and any other data that may be received by sensor 124. In some cases, data relating to an neural state 156 of a user may be received by sensor 124 as described above. In some cases, data relating to an neural state 156 may be received through user input. In some cases, data relating to an neural state 156 may include a temporal element wherein a particular passage of time may indicate a particular neural state 156 such as for example, that a user is asleep. For example, a user may indicate that they will fall asleep at 10:00 pm wherein processor 108 may determine that a user is asleep at 10:00 pm. In some cases, a user may input a sleep schedule of times in which a user may ideally be asleep wherein processor 108 may be configured to determine whether a user is awake or asleep based on the input sleep schedule. In some cases, neural state 156 may be transmitted to database 116. In some cases, database 116 may contain a plurality of user data 152 and/or neural states 156 wherein a researcher, or a computing device may make one or more determinations based on the neural states of multiple users. In some cases, the data may be used to make determinations about particular neural stimulation therapies, such as the effectiveness of the therapies.

With continued reference to FIG. 1, user data may include changes (e.g. improvements or deterioration) associated with the user's neurological disorder. In some cases, the changes may be associated to previous use of apparatus 100. For example, user data may include data relating to previous use of apparatus 100 such as various treatment options on previous iterations and the results of those options. For example, a user may have been given a particular treatment wherein the treatment may have improved the user's neurological disorder, caused further deterioration or had no effect on the user at all. In some cases processor 108 may be configured to receive previous treatments (or commands as described below) and make determinations based on the treatments. For example, processor 108 may make determinations that a previous treatment was not effective and as a result increase the treatment as will be described in further detail below.

With continued reference to FIG. 1, user data 152 may include one or more light patterns 160. A "light pattern" for the purposes of this disclosure is information relating to the intensity of light-emitting device 128, the duration of each pulse of light and the like. In some cases, a user may prefer or benefit from a particular light pattern 160. For example, a user may benefit from a light pattern 160 of 40 hz or 40 flashes per second wherein the particular frequency may aid in photic entrainment. In some cases, a user may benefit from a higher or lower frequency. In some cases, each neurological dysfunction may be associated with a particular frequency of emitting light. In some cases, a user may input the particular neurological dysfunction or the associated light pattern into user data 152. In some cases, a particular light pattern 160 may increase gamma brainwaves and lead to clearing of beta amyloid plaques in the brain, a key abnormality in Alzheimer's disease by encouraging protective cells to phagocytize the harmful proteins that accumulate in the brain.

With continued reference to FIG. 1, in some cases, user data 152 may be received by a user through input. For example, a user may interact with a user interface as described below wherein a user may be prompted to input user data 152. In some cases, user data 152 may be received through a remote device such as a smartphone desktop computer, or laptop. In some cases, user data 152 may include data form files or documents that have been converted into machine-encoded test using an optical character reader (OCR). For example, a user may input digital records and/or scanned physical documents that have been converted to digital documents, wherein user data 152 may include data that have bene converted into machine readable text. In some cases, user data 152 may include medical documents such as medical history, prescriptions and the like. In some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2-4. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2, 3 and 4.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, user data 152 may be received from a user interface, wherein a user may input user data 152 by interacting with the user interface. For example, a user may select options depicted on the interface wherein each option may be inputted as user data 152. In another non-limiting example, a user may answer questions wherein an answer to each question may be input as user data 152.

With continued reference to FIG. 1, processor 108 is configured to generate one or more stimulatory commands 164 as a function of the user data 152. A "stimulatory command" for the purposes of this disclosure is a specific set of instructions given by a computing device and configured to perform a specific task or function. In some cases, stimulatory command 164 may include a command to power on head device 120, power on light-emitting device 128 and/or power on any other devices associated with head device 120. In some cases, stimulatory command 164 may include a command to power on light-emitting device 128 and emit a light. In some cases, stimulatory command 164 may include a command to emit light at a given frequency of wavelength. In some cases, stimulatory command 164 may include a command to emit light at a particular time, in particular intervals and the like. For example, stimulatory command 164 may include a command to emit light at given hours of the day. In some cases, stimulatory command 164 may include a command to activate noise-cancelling capabilities on head device 120 through noise noise-cancelling device 136. In some cases, stimulatory command 164 may include a particular command to power on TFUD 140 device, modify an emitted frequency of TFUD 140 device, modify a pulse duration on TFUD 140 device and/or modify an intensity with TFUD 140 device. In some cases, control module 148 may transmit stimulatory command 164 to one or more devices and modify a plurality of parameters on each device. In some cases, stimulatory command 164 may further include any command capable of controlling one or more parameters of any neural stimulation or photic entrainment devices as described herein. In some cases, stimulatory command 164 may include a command to light-emitting device 128 to emit light with a particular light pattern. For example, stimulatory command 164 may include a command to emit light at a given pulse, intensity, or frequency. In some cases, each stimulatory command 164 may be configured to modify a particular parameter of one or more devices described in this disclosure. In some cases, processor 108 may be configured to generate one or more stimulatory commands 164 wherein multiple devices may operate in synchronization, such as for example, the light-emitting device 128, the TFUD 140 and the TMS device 144 all operating at the same time.

With continued reference to FIG. 1, processor 108 may be configured to generate one or more stimulatory commands 164 based on a user's neurological disorder within user data 152. For example, processor 108 may generate one or more stimulatory commands 164 if a user is suffering from Parkinson's wherein the stimulatory commands 164 are configured to treat dysfunctions associated with Parkinson's disease. In another non-limiting example, processor 108 may generate stimulatory commands 164 used to treat essential tremor when user data 152 indicates that a user suffers from essential tremor. Additionally or alternatively, generating one or more stimulatory commands 164 may be based off of the severity of a user's neurological dysfunction. For example, one or more stimulatory commands 164 may include commands to modify the intensity, pulse, or duration of one or more devices when user data 152 indicates the severity of a particular condition. In some cases, processor 108 may use a lookup table to 'lookup' the associated stimulatory commands 164 associated with one or more neurological diseases. In some cases the lookup table may include a set of stimulatory commands 164 for each neurological disorder and its severity. For example, processor 108 may generate differing stimulatory commands 164 for a user with Parkinson's with a 4 rating, and a user with Parkinson's with a 2 rating. In some cases, stimulatory commands 164 may vary between each level of severity in order to apply the appropriate treatment with respect to the severity of the disorder. For example, a neurological order with a higher severity rating may require more aggressive neurological stimulation techniques. A "lookup table," for the purposes of this disclosure, is a data structure, such as without limitation an array of data, that maps input values to output values. A lookup table may be used to replace a runtime computation with an indexing operation or the like, such as an array indexing operation. A look-up table may be configured to pre-calculate and store data in static program storage, calculated as part of a program's initialization phase or even stored in hardware in application-specific platforms. Data within the lookup table may include one or more stimulatory commands 164 associated with one or more elements within user data 152. Data within the lookup table may be received from database 116. In some cases, database 116 may be populated by an operator, wherein the operator may continuously update commands in database 116. In a non-limiting example, processor 108 may look up a particular stimulatory command 164 using the neurological disorder within user data 152 and its corresponding rating.

In some cases, processor 108 may be configured to generate one or more stimulatory commands 164 using a rule-based system. "Rule-based system" also known as "rule-based engine" "rule-based engine" is a system that executes one or more rules such as, without limitations, such as a command rule in a runtime production environment. As used in this disclosure, a "command rule" is a pair including a set of conditions and a set of actions, wherein each condition within the set of conditions is a representation of a fact, an antecedent, or otherwise a pattern, and each action within the set of actions is a representation of a consequent. In a non-limiting example, command rule may include a condition of "when user data 152 includes X" pair with an action of "generate one or more support stimulatory commands 164 associated with X." In some embodiments, rule-based engine may execute one or more command rules on data if any conditions within one or more command rules are met. In some embodiments, command rule may be stored in a database 116 as described in this disclosure. In some cases, command rule may include a rule such as "If the rating of a condition is higher than X" and a corresponding action indicating "increase the intensity of one or more stimulatory commands 164 by a factor of X". In some cases, processor 108 may receive user data 152 and make calculations using an arithmetic logic unit within computing device. For example processor 108 may calculate the settings (e.g. intensity, pulse, duration, frequency etc.) for each device by using parameters given with user data 152. For example, processor 108 may receive one or more formulas and input the users age, height, weight, neurological disorder, severity of the neurological disorder and/or any other information within user data 152 to generate one or more stimulatory commands 164. For example, a male with a particular neurological disorder may be given stimulatory commands 164 differing from a female with the same disorder. Similarly, a child or an elderly individual may be given one or more stimulatory commands 164 that differ from the commands given to an adult. In some cases, stimulatory commands 164 may differ amongst sexes or ages due to biological traits that may affect users differently. In some cases, database 116 may be populated with one or more formulas, wherein each formula may be used for a particular neurological disorder. In some cases formulas within database 116 may be generated by a user, wherein processor 108 may generate one or more stimulatory commands 164. In some cases, processor 108 each formula may be associated with each stimulatory command 164. In some cases, processor 108 may generate formulas using linear regression. "Linear regression" for the purposes of this disclosure is a method of predicting a variable based on value of another associated variable. For example, processor 108 may receive stimulatory commands 164 associated with a 45-year-old and commands associated with a 60-year-old wherein processor 108 may perform linear regression to determine a particular stimulatory command 164 for a 55-year-old. In some cases, processor 108 may take known stimulatory commands 164 and use linear regression to generate stimulatory commands 164 of individuals with differing variables, such as differing age, differing severity and the like.

With continued reference to FIG. 1, processor 108 may generate one or more stimulatory commands 164 using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, computing device may generate a web crawler to generate one or more stimulatory commands 164. The web crawler may be seeded and/or trained with a reputable website, such as research sites relates to neurological disorders, government sites and the like to begin the search. A web crawler may be generated by computing device. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract any data suitable for one or more stimulatory commands 164. In some cases, the web crawler can be trained to extract stimulatory data from one or more websites, wherein the stimulatory data contains any information that processor may use to generate one or more stimulatory commands. In some cases, the web crawler may be configured to receive one or more elements within user data wherein processor 108 may be configured to generate one or more stimulatory commands in any way as described in this disclosure. In some cases, the web crawler may be configured to modify and/or repopulate a lookup table wherein the lookup table may contain updated stimulatory commands 164 such as updated frequencies for emitting sound or vibrations. In some cases, the WebCrawler may be configured to receive newly published information relating to neural stimulation wherein processor 108 may be configured to generate one or more stimulatory commands based on the newly retrieved information.

With continued reference to FIG. 1, processor 108 may be configured to generate one or more stimulatory commands 164 based on previous treatments given to a user on a previous iteration or other stimulation devices. In some cases, processor may be configured to receive input based on previous iterations wherein processor may make determinations based on previous treatments given. For example, processor 108 may be configured to increase the frequency of one or more devices as described in this disclosure when user input and/or user data indicates that a previous treatment plan was not effective. In some cases, processor may be configured to lower the frequency when user input and/or user data indicates that a previous treatment plan containing one or more stimulatory commands contained commands at too high of a frequency. In some cases, processor may generate one or more stimulatory commands and modify the one or more stimulatory commands based on previous treatments or previous iterations associated with the same user. For example, processor may be configured to modify one or more stimulatory commands 164 as a function of a multiplier when user data 152 and/or user input indicates that a previous stimulatory command was not effective.

With continued reference to FIG. 1, generating one or more stimulatory commands 164 includes determining the neural state 156 of a user. Processor 108 may receive information relating to the neural state 156 of a user and make determinations such as whether a user is awake or asleep, determinations about a user's brain activity in response to various neural stimuli, and the like. For example, processor 108 may determine that a user is awake based on the received beats per minute associated with the user. In some cases, processor 108 may receive a temperature of the user wherein processor 108 may determine if a user is awake or asleep based on the user's body temperature. Processor 108 may receive data points, wherein the data points comprises information indicating at what temperature, heart rate and the like a user may be awake or asleep. Processor 108 may compare elements within user data 152 to the data points to determine if the user is awake or asleep. In a non-limiting example, a data point may indicate that a heart rate above 80 may indicate that a user is awake, wherein processor 108 may receive the heart rate form user data 152 and compare it to the data point to determine if the user is awake. In some cases, processor may determine if a user is awake or asleep based on user input, wherein processor 108 may determine if the user is asleep based on the user's input sleep schedule. In some cases, processor 108 may use machine vision system to make one or more determinations about the unconscionability of a user. For example, machine vision system may be configured to determine if a user's eyes are closed for a predetermined period of time, wherein processor 108 may determine that the user is asleep. Similarly, machine vision system may determine that a user is awake based on the user's eyes being open.

With continued reference to FIG. 1, determining the neural state 156 of a user may include determining a particular change in voltage associated with a user's neural activity. In some cases, determining neural state may further include determining hemoglobin-concentration changes in the brain based on optical intensity measurements. In some cases, determining the neural state 156 of a user may include determining changes in blood oxygen levels in the brain and/or changes in blood flow to the brain. In some cases, determining neural state 156 may include determining changes in concentration of various vital neural elements within the brain such as oxygen level, hemoglobin level and the like. In some cases, processor 108 may be configured to receive a previous neural state of a user wherein the previous neural state may include a neural state 156 generated on a different iteration of the processing such as a different time or day. In some cases, processor 108 may be configured to receive one or more stimulatory commands using a lookup table wherein a particular change in neural activity may indicate a particular stimulatory command 164. For example, a particular hemoglobin concentration or change in hemoglobin concentration may indicate a particular stimulatory command 164. Similarly, a neural state 156 may indicate a particular oxygen level wherein a particular stimulatory command may be associated with the particular oxygen level. In some cases, processor 108 may be configured to transmit the neural state 156 to database 116 wherein determinations can be made from a plurality of user's and their corresponding neural state 156. In some cases, processor 108 may make calculations wherein a particular change in a user's neural activity may be correlated to a specific stimulatory command 164.

With continued reference to FIG. 1, processor 108 may be configured to cease transmission of one or more stimulatory commands 164 based on the neural state 156 of a user. For example, processor 108 may determine that a user is awake wherein processor 108 may determine that the stimulatory commands 164 should not be sent until a user is asleep. In some cases, processor 108 may delay the transmission of one or more stimulatory commands 164 based on whether the user is awake or asleep. In an embodiment, a user may elect to not receive neural stimulation from apparatus 100 until the user has fallen asleep. In some cases, the presence of sounds and lights may inhibit a user from falling asleep. As a result, processor 108 may be configured to first determine whether a user is asleep prior to transmitting one or more stimulatory commands 164. In some cases, processor 108 may determine that only particular commands of the one or more stimulatory commands 164 may be transmitted when a user is awake. For example, processor 108 may transmit a stimulatory command 164 to activate noise-cancelling device 136 wherein noise-cancelling device 136 may help a user fall asleep. In some cases, processor 108 may be configured to modify one or more stimulatory commands 164 if a user is awake. For example, processor 108 may be configured to modify a stimulatory command 164 such that a light emitted from light-emitting device 128 may contain a lower lux, or an audio from audio-output device is minimized until the user falls asleep. In some cases, processor 108 may be configured to receive one or more formulas from database 116 that indicate the fraction of intensities relating to one or more stimulatory commands 164 when a user is awake. In some cases, processor 108 may be configured to delay one or more stimulatory commands 164 until a user is asleep. In some cases, undergoing treatment by apparatus 100 may be difficult when a user is awake. This may be due to the lights being emitted, the sounds being emitted and any other emissions that may cause a nuisance to the user. As a result, a user may feel dissuaded from interacting with apparatus 100. In some cases, processor 108 may be configured to determine if a user is awake or asleep in order to reduce the nuisance that may be associated with the emissions and only emit when the user is asleep.

With continued reference to FIG. 1, generating one or more stimulatory commands 164 includes generating one or more stimulatory commands 164 using a stimulatory machine learning model 168. Processor 108 may use a machine learning module, such as a stimulatory machine learning module for the purposes of this disclosure, to implement one or more algorithms or generate one or more machine-learning models, such as an assessment machine learning model, to calculate at least one smart assessments. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, such as any database 116 described in this disclosure, or be provided by a user. In other embodiments, a machine-learning module may obtain a training set by querying a communicatively connected database 116 that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more stimulatory commands 164 corresponding to categories of data elements. As a non-limiting example, training data may include data entered in standardized forms by persons or processes, such that entry of a given data element in a given field in a form may be mapped to one or more categories. Elements in training data may be linked to categories by tags, tokens, or other data elements. A machine learning module, such as stimulatory module, may be used to generate stimulatory machine learning model 168 and/or any other machine learning model described herein using training data. Stimulatory machine learning model 168 may be trained by correlated inputs and outputs of training data. Training data may be data sets that have already been converted from raw data whether manually, by machine, or any other method. Stimulatory training data 172 may be stored in database 116. Stimulatory training data 172 may also be retrieved from database 116.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from database 116, such as any database 116 120 described in this disclosure, or be provided by a user such as a physician, insurance provider, and the like. In other embodiments, machine-learning module may obtain a training set by querying a communicatively connected database 116 120 that includes past inputs and outputs. Training data may include inputs from various types of databases, resources, and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more support modules 132 corresponding to categories of data elements. As a non-limiting example, training data may include data entered in standardized forms by persons or processes, such that entry of a given data element in a given field in a form may be mapped to one or more categories. Elements in training data may be linked to categories by tags, tokens, or other data elements.

With continued reference to FIG. 1, generating one or more stimulatory commands 164 may include receiving stimulatory training data 172. stimulatory training data 172 may include a plurality of user data 152 correlated to a plurality of stimulatory commands 164. In an embodiment, stimulatory training data 172 may be used to show that a particular user data 152 may be associated with one or more stimulatory commands 164. In some cases, stimulatory training data 172 may be received from a user, third party, database 116, external computing devices previous iterations of the processing and/or the like as described in this disclosure. In some cases, stimulatory training data 172 may include previous iterations of user data 152 and one or more stimulatory commands 164. In some cases, generating one or more stimulatory commands 164 further includes training stimulatory machine learning model 168 as a function of the stimulatory training data 172 and generating one or more stimulatory commands 164 as a function of the stimulatory machine learning model 168. In some cases, stimulatory machine learning model 168 may be trained by user feedback. For example, a user may provide feedback that a particular stimulatory command 164 helped treat the user's neurological condition while another aggravated it. In some cases, user feedback may be used to train stimulatory machine learning model 168 in order to provide more accurate stimulatory commands 164 in future iterations.

With continued reference to FIG. 1, generating one or more stimulatory commands 164 may include generating one or more stimulatory commands 164 based on user input. For example, a user may interact with a user interface wherein a user may select options on the user interface that may signify to processor 108 to generate a particular stimulatory command 164. Continuing, a user may select one or more options relating to light-emitting device 128 in order to operate light-emitting device 128 and alter one or more settings. For the purposes of this disclosure, a "user interface" is a means by which a user and a computer system interact. For example a user may interact with a computer system through the use of input devices and software wherein user interface may be configured to facilitate the interaction between the user and the computer system. A user interface may include graphical user interface, command line interface (CLI), menu-driven user interface, touch user interface, voice user interface (VUI), form-based user interface, any combination thereof and the like. In some embodiments, a user may interact with the user interface using a computing device 104 distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. Persons skilled in the art, upon reviewing the entirety of this disclosure, will be aware of various ways in which a graphical user interface and/or elements thereof may be implemented and/or used as described in this disclosure. In some cases, a user may interact with GUI, wherein user input may be used to generate one or more stimulatory commands 164. In some cases, processor 108 may generate one or more stimulatory commands 164 and present them to a user through a GUI, wherein a user may modify or accept the stimulatory commands 164 to be transmitted to head device 120.

With continued reference to FIG. 1, processor 108 is configured to transmit one or more stimulatory commands 164 to head device 120. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed by head device 120 from database 116. In some cases, control module 148 may be configured to receive one or more stimulatory commands 164 from database 116 or through wired or wireless transmission.

With continued reference to FIG. 1, control module 148 may be configured to receive one or more stimulatory commands 164 and operate at least light-emitting device 128 as a function of the one or more stimulatory commands 164 as described above. In some cases, control module 148 may convert the stimulatory commands 164 into control signals to control one or more devices as described in this disclosure. In some cases, control module 148 may be configured to emit a light from light-emitting device 128, stop the emission of a light from light-emitting device 128, alter the frequency of the light emitted from light-emitting device 128 and the like.

With continued reference to FIG. 1, apparatus 100 may be configured for co-administration with intravenous infusion therapy. "Intravenous infusion therapy," for the purposes of this disclosure, is the receiving of medication through a needle into the body of a user. In some cases, intravenous infusion therapy may allow for immediate infusion of a particular medication into a user's bloodstream. In some cases intravenous infusion therapy may include the use of an anti-amyloid drug. The anti-amyloid drug may be used to lower the amount of beta-amyloid (or amyloid plaques) in a user's brain. In some cases, intravenous infusion therapy may be used to reduce or prevent the build of plaque in a user's brain and thereby treat neurological conditions associated with the build up of plaque such as Alzheimer's. In some cases, the anti-amyloid drug may include, but is not limited to, Aducanumab and Lecanemab, two drug configured to target plaque and reduce plaque buildup in a user's brain. In some cases, apparatus 100 may be configured for co-administration with other plaque staining agents such as methylene blue or other novel neural small molecule compounds such as AqLNMNo2. In some cases, coadministration with intravenous infusion therapy may help increase the removal of plaque in the brain. In some cases, apparatus 100 may increase the efficacy of plaque staining agents by facilitating the delivery of the plaque staining agents to various areas of the user's brain. In some cases, co-administration may allow treatment of a neurological disorder using two or more techniques to help treat the disorder. In an embodiment, co-administration may allow for more effective treatments, or multiple treatments. In some cases, apparatus 100 may allow for neural stimulation using multiple devices. In addition, apparatus 100 may be configured for co-administration of multiple neural stimulation devices such as photic entrainment stimuli emitted by light-emitting device 128, auditory stimuli emitted by audio output device 132 and the like. In some cases, user data may include information relating to a co-administrative use of one or more intravenous medications as described above. In some cases, processor 108 may be configured to generate one or more stimulatory commands 164 as a function of the medications. In some cases, processor 108 may retrieve one or more stimulatory commands 1645 from a database 116, wherein the one or more stimulatory commands 164 are associated with a particular medication. In some cases, database 116 may be populated with a plurality of stimulatory commands, each associated with a particular medication. In some cases, processor 108 may be configured to retrieve the appropriate stimulatory commands 164 associated with the medication. In some cases, co-administration of a particular medication along with neural stimulation of one or more devices as described in this disclosure may aid in the improvement of neurological disorders.

Figure 2:
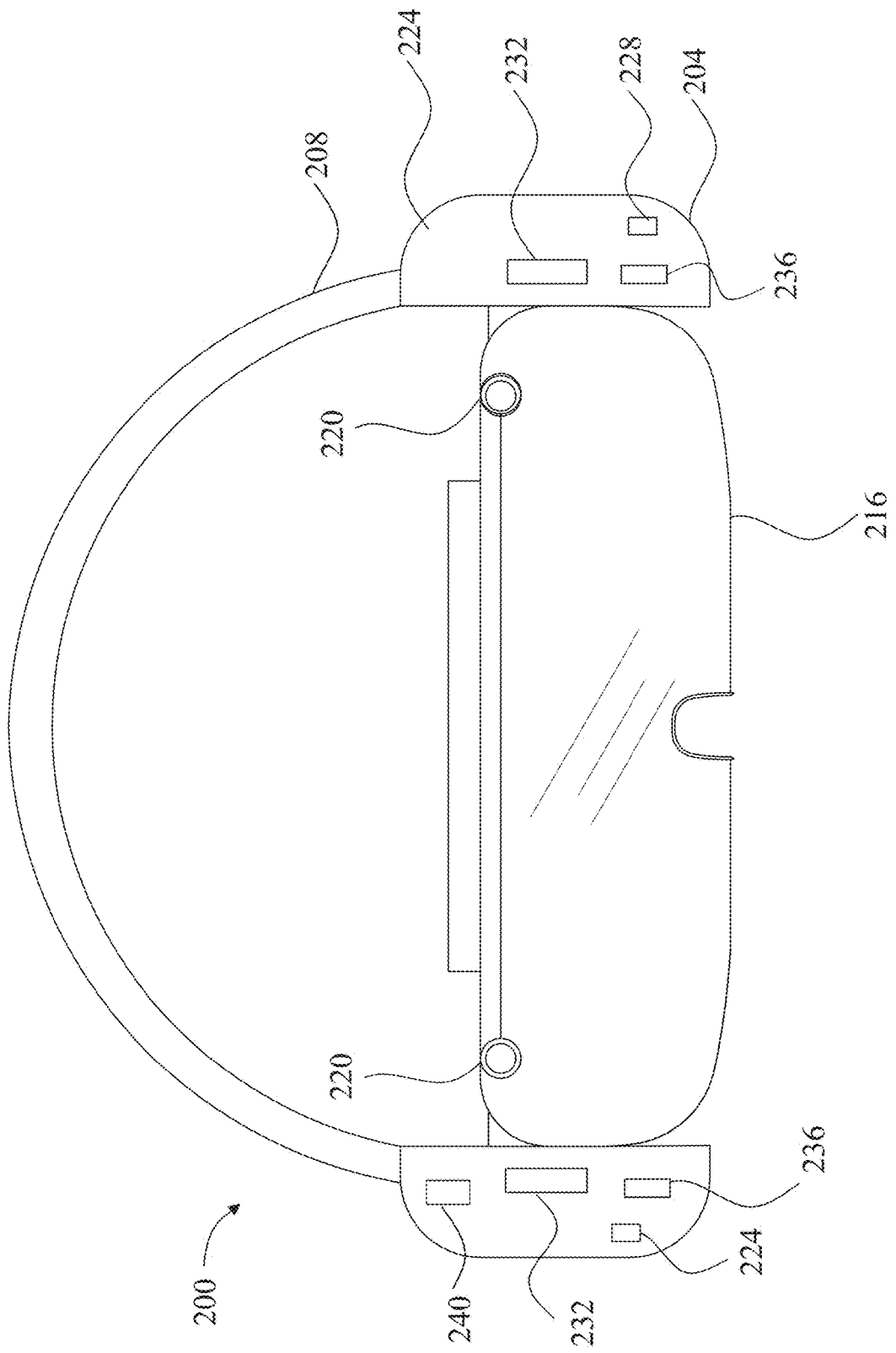
FIG. 2 is an exemplary embodiment of a head device in accordance with the subject disclosure.

Referring now to FIG. 2, an exemplary embodiment of a head device 200 is described ins accordance with the subject disclosure. In some cases, head device may include a housing 204 to hold one or more components together. In some cases, the housing 204 may contain a head band 208 configured to be placed over the head of a user. the head band 208 may extend from one section of a user's head towards another section of the user's head. In some cases the head band 208 may provide for placement of head device on a head of a user without any external support. In some cases, head band 208 may further allow for head device 200 to be used when a user is unconscious or performing other tasks. In some cases, head band 208 may provide for one or more components of head device to be situated next to the skull of a user for optical neural stimulation. In some cases, head device may include a screen 216 situated in front of the eyes of a user. In some cases, the screen may be transparent wherein a user may be able to view surrounding area through screen 216. In some cases, screen 216 may be configured to block out surrounding light similar to sunglasses. In some cases, screen may be opaque wherein screen may be configured to prevent surrounding light from entering the eyes of a user. In some cases, screen may be used to help a user fall asleep. In some cases, head device 200 may further include one or more light emitting devices 220. The light emitting devices may be situated directly in front of, or near the eyes of the user. The light emitting devices may be consistent with any light emitting devices as described in this disclosure. In some cases, light emitting devices 220 may be placed on screen 216. In some cases, screen 216 may prevent outside light from entering the eyes of a user, wherein light emitting devices 220 may instead emit a light. In some cases, head device may further include an audio-output device 224. Audio-output device 224 may be in the form of speakers, earphones, headphones and the like. in some cases, audio-output device 224 may be situated directly on top of or near the ears of a user. In some cases, audio-output 224 device may provide neural stimulation through one or more stimulatory commands as described above.

With continued reference to FIG. 2, in some cases, head device may further include a sensor 228. Sensor 228 may be configured to retrieve any data as described above. In some cases, sensor 228 may include a microphone wherein the microphone is configured to receive background noises. In some cases, a computing device may receive background noises from sensor 224 as noise signals and emit inverted noise signals through audio-output device 224 wherein the inverted noise signals may cancel out incoming background noise. In some cases, noise cancelling device as described above may include audio-output device 224 and sensor 228. In some cases, head device 200 may further include a transcranial focused ultrasound device (TFUD) 232 configured to provide neural stimulation to a user through the use of low intensity sound waves. Ultrasound waves non-invasively to various regions of a user's brain. In some cases, low intensity ultrasound waves may be focused onto various areas of a user's brain. In some cases, ultrasound waves may be configured to allow for penetration of areas in the brain that may not be accessed without invasive procedures. In some cases, TFUD 232 may be configured to emit one or more ultra sound waves as a function of one or more stimulatory commands.

With continued reference to FIG. 2, In some cases, head device 200 may further include a transcranial magnetic stimulation (TMS) device 236 configured to modulate brain activity using magnetic field to stimulate nerve cells in the brain. In some cases, TMS device 236 may provide for treatment of neurological disorders such as obsessive-compulsive disorder, depression, addiction, and the like. In some cases, TMS device 236 may include a magnetic coil, wherein the magnetic coil is configured to be placed on the scalp of a user's head and provide magnetic pulses to various regions of a user's brain. In some cases, TMS device 236 may emit a single pulse or a series of pulses wherein the pulses may vary in frequency and duration. In some cases, the pulses may vary in frequency below 1 Hz, wherein the pulses may be configured to inhibit cortical firing whereas as frequency of greater than 1 Hz may be configured to increase cortical firing. In some cases, pulses emitted from TMS device 236 may be modified as aa function of or more stimulatory commands as described above.

With continued reference to FIG. 2, head device 200 may further include a control module 240. Control modules 240 may be consistent with any control module 240 as described in this disclosure. In some cases, cases control module 240 may include a computing device. In some cases, control module may be configured to control any devices (e.g. audio-output device 204, TMS device, 236, TFUD 232, light emitting device 220, etc.) such as by modifying a frequency, a pulse and the like from the devices. In some cases, control module 240 may be configured to convert the one or more stimulatory commands into electrical signals. Ins some cases, control module 240 may receive data and output commands to control the devices on head device 200.

Figure 3:
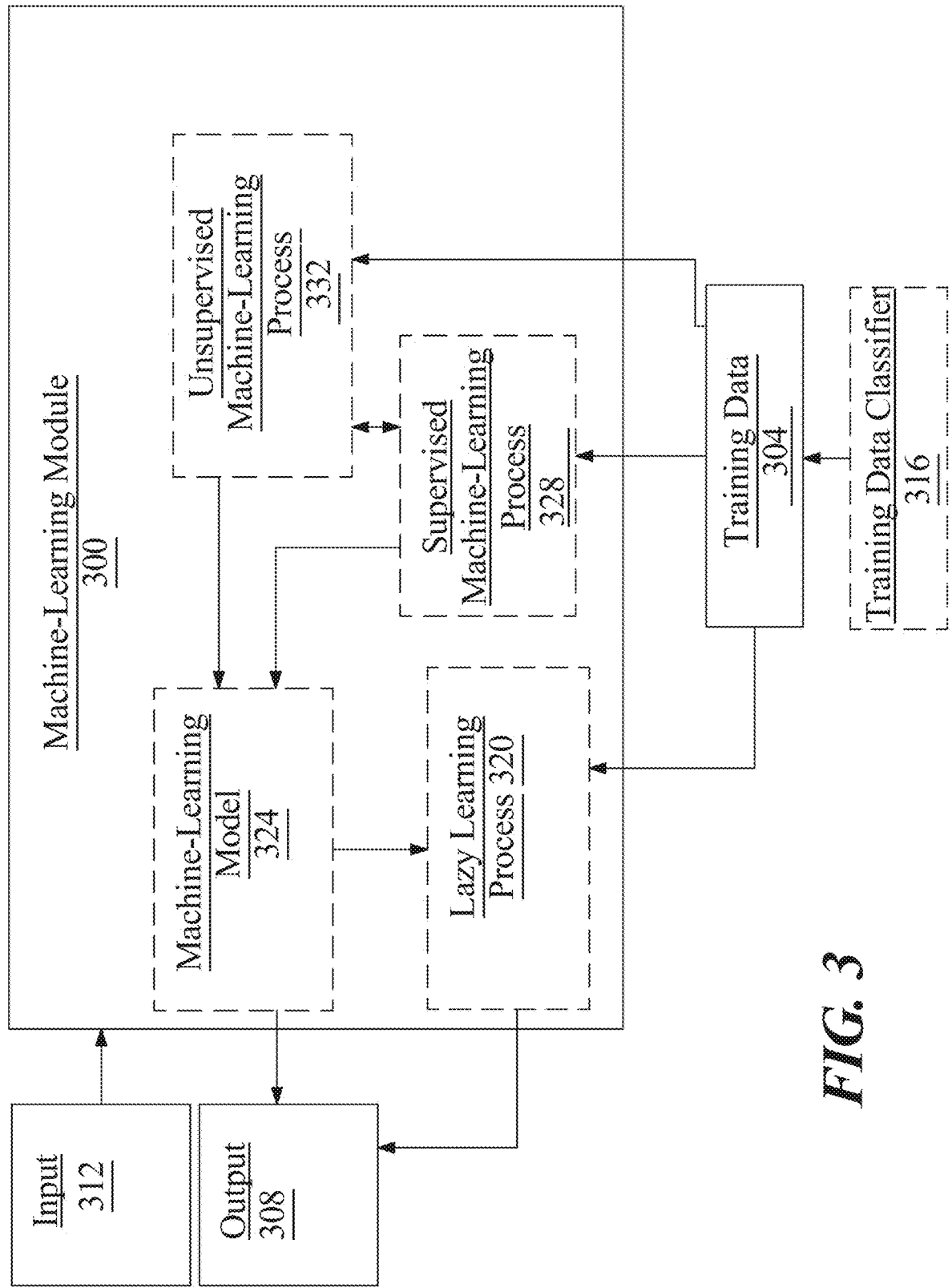
FIG. 3 is a block diagram of exemplary embodiment of a machine learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to subsets of neurological diseases, such as categorization referring to depression, Alzheimer's, Parkinson's and the like for which a subset of training data may be selected.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include user data as described above as inputs, stimulatory commands as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 4:
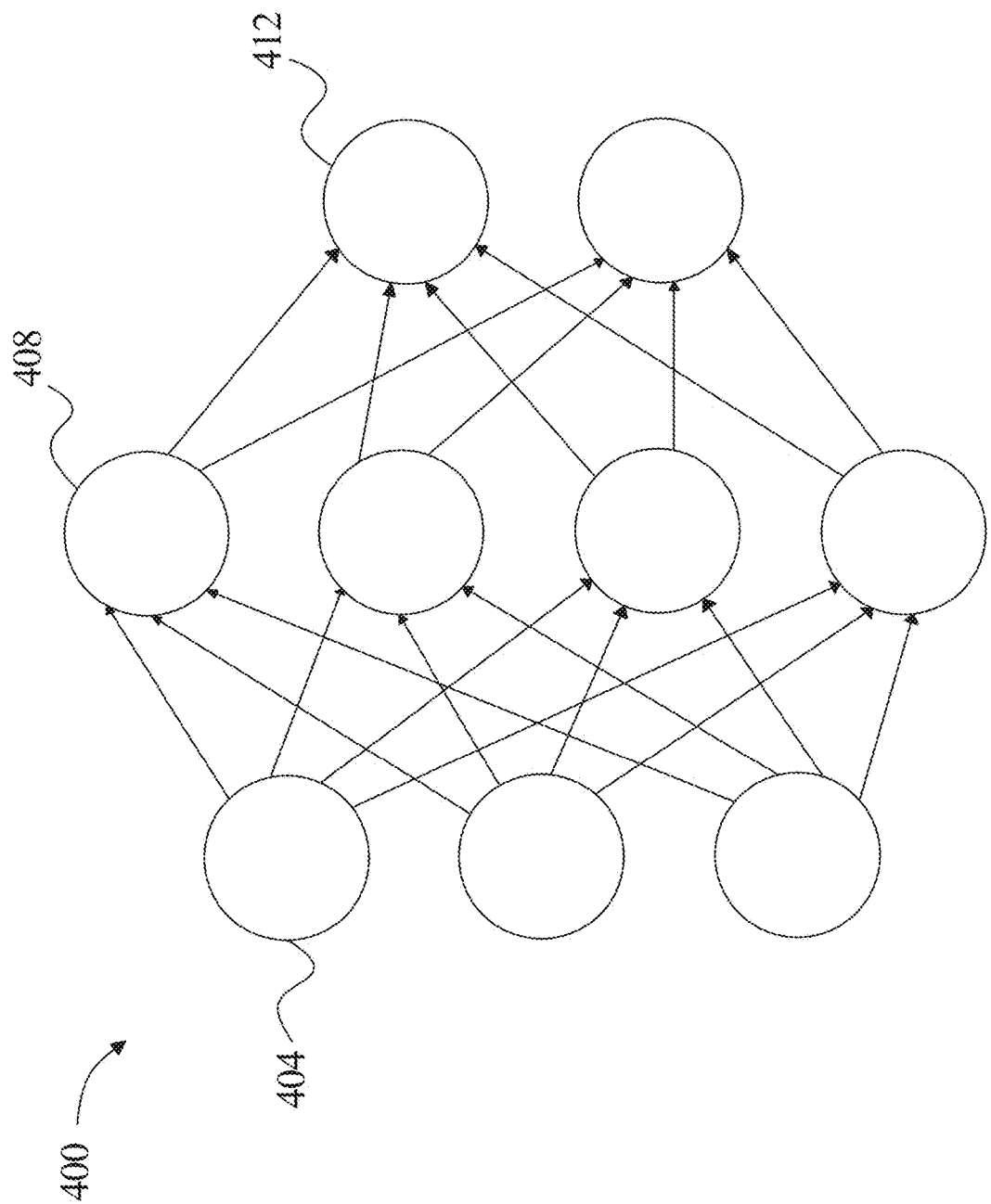
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
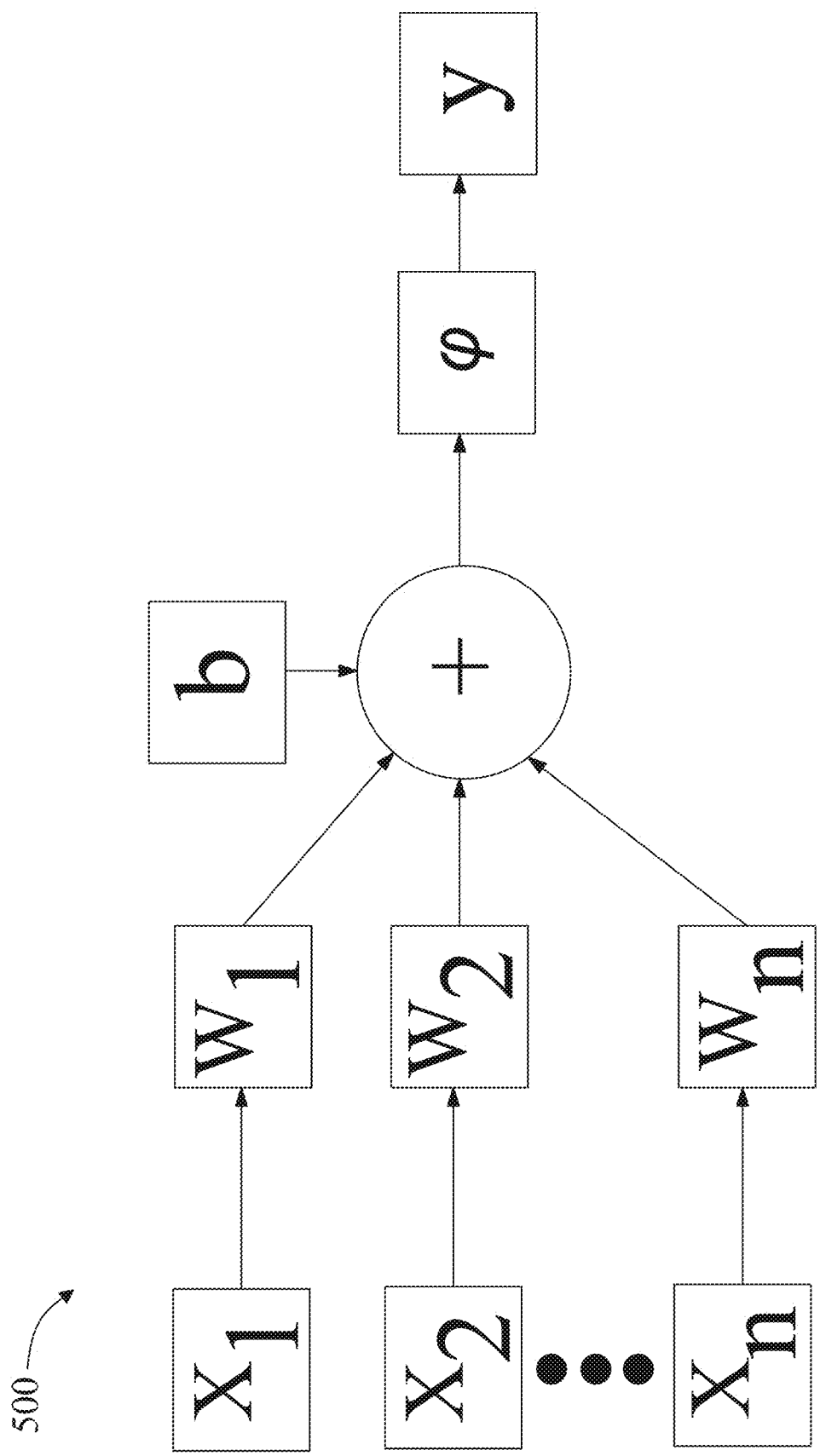
FIG. 5 is a block diagram of an exemplary embodiment of a node.

Referring now to FIG. 5, an exemplary embodiment of a node 500 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
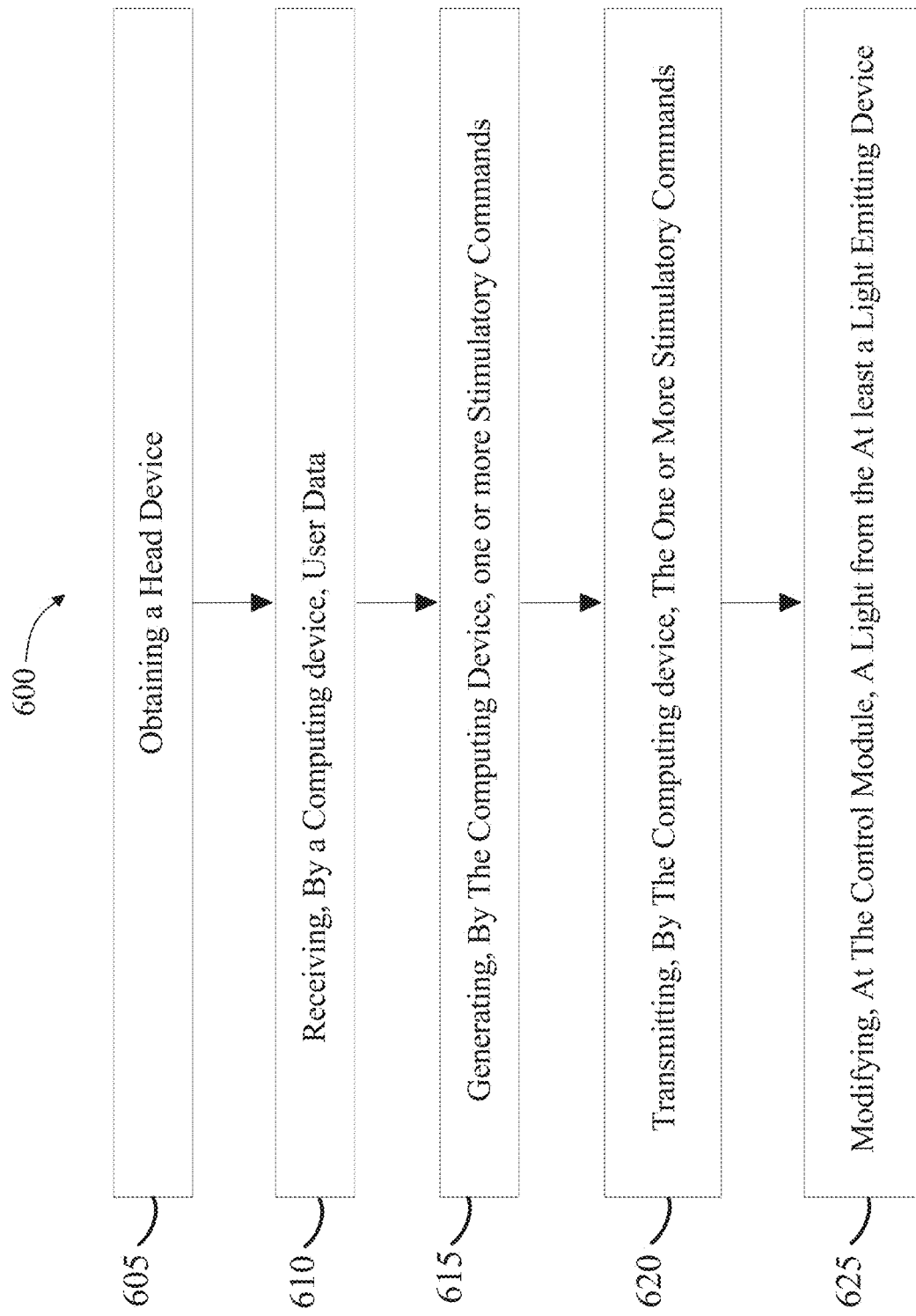
FIG. 6 is a flow diagram illustrating an exemplary embodiment of a method for neural stimulation.

Referring now to FIG. 6, a method 600 for neural stimulation is described. At step 605, method 600 includes obtaining a head device configured to be worn on the head of a user. The head device includes a light emitting device configured to provide photic entrainment to a user. The head device further includes a control module. In some cases, head device may include an audio output device, the audio output device configured to provide neural stimulation to the user as a function of one or more stimulatory commands. In some cases, the head device further includes a noise cancelling device, the noise cancelling device configured to reduce background noise associated with the user. In some cases, the head device further includes a transcranial focused ultrasound device (TFUD), the TFUD configured to provide neural stimulation to the user as a function of one or more stimulatory commands. In some cases, the head device further includes a transcranial magnetic stimulation device (TMS), the TMS configured to provide magnetic pulses to the brain of a user as a function of the one or more stimulatory commands. This may be implemented with reference to FIGS. 1-6 and without limitation.

With continued reference to FIG. 6, at step 610 method 600 includes receiving, by a computing device communicatively connected to the head device, user data wherein the user data includes information relating to a neural state of a user. In some cases, the user data further includes one or more light patterns. This may be implemented with reference to FIGS. 1-6 and without limitation.

With continued reference to FIG. 6, at step 615 method 600 includes generating, by the computing device, one or more stimulatory commands wherein generating includes determining the neural state of the user. In some cases, generating, by the computing device, the one or more stimulatory commands as a function of the user data further includes receiving stimulatory training data having a plurality of user data correlated to a plurality of stimulatory commands, training a stimulatory machine learning model as a function of the stimulatory training data, and generating the one or more stimulatory commands as a function of the stimulatory machine learning model. This may be implemented with reference to FIGS. 1-6 and without limitation.

With continued reference to FIG. 6, at step 620, method 600 includes transmitting, by the computing device, one or more stimulatory commands to the head device. This may be implemented with reference to FIGS. 1-6 and without limitation.

With continued reference to FIG. 6, at step 625, method 600 includes modifying, at the control module, a light from the at least the light emitting device. In some cases, control module may be configured to modify a light from light emitting device may modifying the frequency, pulse duration, and intensity of the light emitted from light emitting device. In some cases, control module may be configured to turn on and off light emitting device. In some cases, control module may further be configured to modify parameters and/or settings associated with one or more devices as described in this disclosure. For example, control module may be configured to modify the pulse of TFUD, the frequency of TFUD, the Frequency of audio-output device and the like. In some cases, method 600 may further include co-administering an intravenous infusion therapy. In some cases, the user data comprises information relating to a co-administrative use of one or more intravenous medications. In some cases, generating one or more stimulatory commands further includes generating one or more stimulatory commands as a function of the co-administrative use. This may be implemented with reference to FIGS. 1-6 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
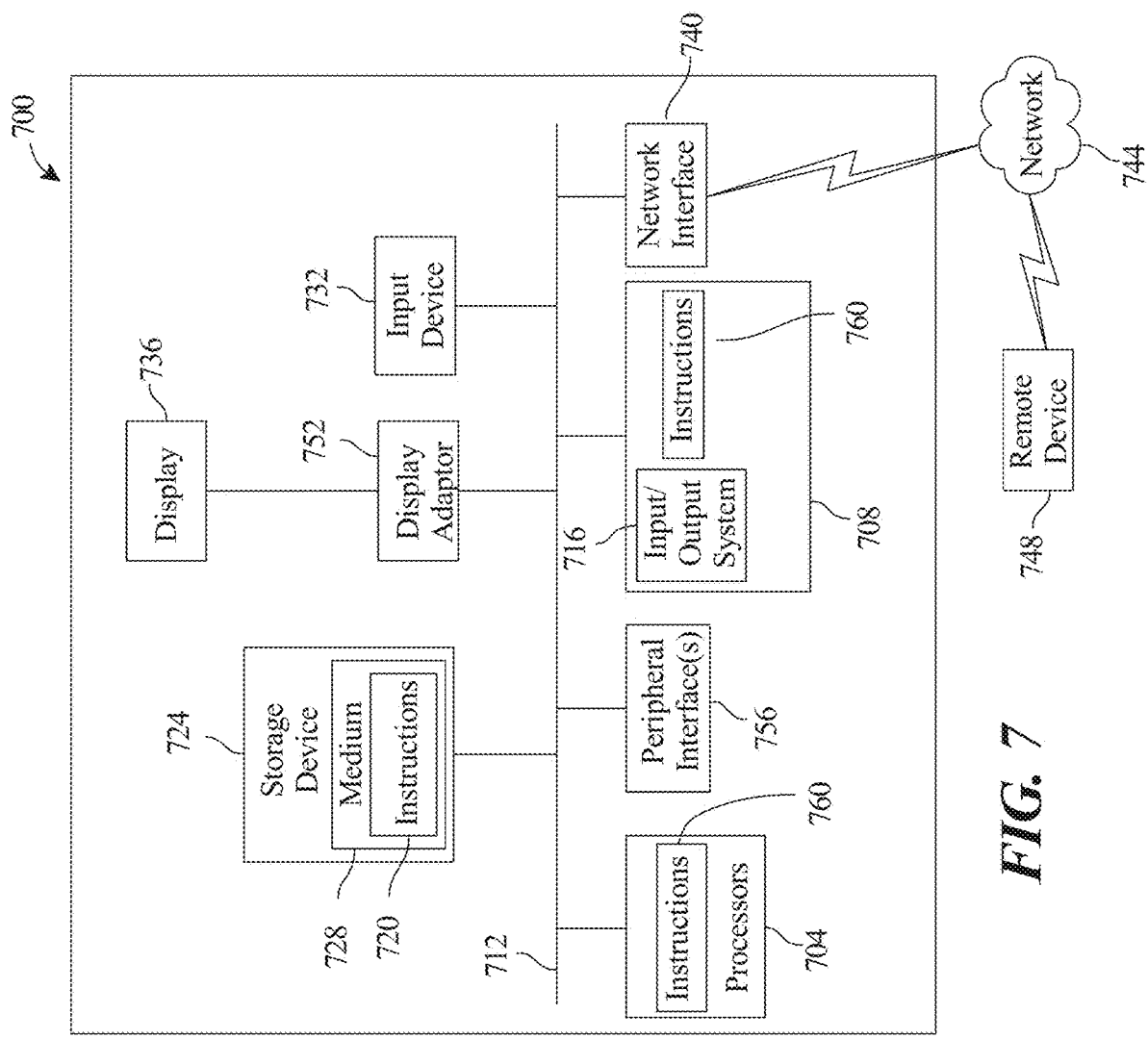
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light-emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for neural stimulation, the apparatus comprising:
   a head device configured to be worn on a head of a user, the head device comprising:
   an opaque screen configured to prevent outside light from reaching eyes of the user;
   at least one light-emitting device configured to provide photic entrainment to the user, wherein the at least one light-emitting device is integrated with the opaque screen;
   at least one control module electrically connected to the at least one light-emitting device and configured to receive one or more stimulatory commands, wherein the at least one control module is configured to operate the at least one light-emitting device as a function of the one or more stimulatory commands; and
   at least one transcranial focused ultrasound device (TFUD), the at least one TFUD configured to provide neural stimulation to the user as a function of the one or more stimulatory commands; and
   at least one computing device communicatively connected to the head device, the at least one computing device comprising;
   a processor; and
   a memory communicatively connected to the processor, the memory containing instructions configuring the processor to:
   receive user data, wherein the user data comprises information relating to a neural state of the user;
   generate the one or more stimulatory commands as a function of the user data, wherein generating the one or more stimulatory commands comprises determining the neural state of the user and using the neural state and/or a user input to determine whether the user is awake or asleep; and
   transmit the one or more stimulatory commands to the head device, wherein the one or more stimulatory commands comprise a command to power on the at least one light-emitting device to provide photic entrainment to the user when the user is determined to be asleep and/or to power on the at least one TFUD and provide neural stimulation to the user when the user is determined to be asleep.

2. The apparatus of claim 1, wherein the head device further comprises at least one audio output device, the at least one audio output device configured to provide neural stimulation to the user as a function of the one or more stimulatory commands.

3. The apparatus of claim 1, wherein the head device further comprises at least one noise cancelling device, the at least one noise cancelling device configured to reduce background noise associated with the user.

4. The apparatus of claim 1, wherein the user data further comprises one or more light patterns.

5. The apparatus of claim 1, wherein generating the one or more stimulatory commands as a function of the user data further comprises receiving one or more stimulatory commands as a function of a machine learning model.

6. The apparatus of claim 1, wherein generating the one or more stimulatory commands as a function of the user data further comprises:
   receiving stimulatory training data comprising a plurality of user data correlated to a plurality of stimulatory commands;
   training a stimulatory machine learning model as a function of the stimulatory training data; and
   generating the one or more stimulatory commands as a function of the stimulatory machine learning model.

7. The apparatus of claim 1, wherein the user data comprises information relating to a co-administrative use of one or more intravenous medications, and wherein the generating the one or more stimulatory commands further comprises generating one or more stimulatory commands as a function of the co-administrative use.

8. The apparatus of claim 1, wherein the head device further comprises at least one transcranial magnetic stimulation (TMS) device, the at least one TMS device configured to provide magnetic pulses to brain of the user as a function of the one or more stimulatory commands.

9. A method for neural stimulation, the method comprising:
   obtaining a head device configured to be worn on a head of a user, the head device comprising:
   an opaque screen configured to prevent outside light from reaching eyes of the user;
   a light-emitting device configured to provide photic entrainment to the user, wherein the light-emitting device is integrated with the opaque screen;
   a control module; and
   at least one transcranial focused ultrasound device (TFUD);
   receiving, by a computing device communicatively connected to the head device, user data wherein the user data comprises information relating to a neural state of the user;
   generating, by the computing device, one or more stimulatory commands, wherein generating the one or more stimulatory commands comprises:
   determining the neural state of the user and using the neural state and/or a user input to determine whether the user is awake or asleep;
   transmitting, by the computing device, the one or more stimulatory commands to the head device; and
   modifying, at the control module, a light from the light-emitting device; and
   providing, by the at least one TFUD, neural stimulation to the user as a function of the one or more stimulatory commands,
   wherein the one or more stimulatory commands comprise a command to power on the light-emitting device to provide photic entrainment to the user when the user is determined to be asleep and/or to power on the at least one TFUD and provide neural stimulation to the user when the user is determined to be asleep.

10. The method of claim 9, wherein the head device further comprises at least one audio output device, the at least one audio output device configured to provide neural stimulation to the user as a function of the one or more stimulatory commands.

11. The method of claim 9, wherein the head device further comprises at least one noise cancelling device, the at least one noise cancelling device configured to reduce any background noise associated with the user.

12. The method of claim 9, wherein the user data further comprises one or more light patterns.

13. The method of claim 9, wherein generating, by the computing device, the one or more stimulatory commands as a function of the user data further comprises receiving one or more stimulatory commands as a function of a machine learning model.

14. The method of claim 9, wherein generating, by the computing device, the one or more stimulatory commands as a function of the user data further comprises:
receiving stimulatory training data comprising a plurality of user data correlated to a plurality of stimulatory commands;
training a stimulatory machine learning model as a function of the stimulatory training data;
and generating the one or more stimulatory commands as a function of the stimulatory machine learning model.

15. The method of claim 9, wherein:
the user data comprises information relating to a co-administrative use of one or more intravenous medications; and
generating the one or more stimulatory commands further comprises generating one or more stimulatory commands as a function of the co-administrative use.

16. The method of claim 9, wherein the head device further comprises at least one transcranial magnetic stimulation (TMS) device, the at least one TMS device configured to provide magnetic pulses to a brain of the user as a function of the one or more stimulatory commands.

17. The apparatus of claim 1, wherein the processor is configured to cease transmission of the one or more stimulatory commands when the user is determined to be awake.

* * * * *